(12) United States Patent
Löffert et al.

(10) Patent No.: US 8,637,288 B2
(45) Date of Patent: Jan. 28, 2014

(54) THERMOSTABLE CHIMERIC NUCLEIC ACID POLYMERASES AND USES THEREOF

(75) Inventors: Dirk Löffert, Düsseldorf (DE); Andreas Missel, Düsseldorf (DE); Jie Kang, Mettmann (DE)

(73) Assignee: Qiagen, GmbH, Hilden (DE)

( * ) Notice: Subject to any disclaimer, the term of this patent is extended or adjusted under 35 U.S.C. 154(b) by 0 days.

(21) Appl. No.: 10/216,682

(22) Filed: Aug. 8, 2002

(65) Prior Publication Data

US 2003/0138805 A1 Jul. 24, 2003

Related U.S. Application Data

(63) Continuation of application No. PCT/EP01/01790, filed on Feb. 16, 2001, which is a continuation-in-part of application No. 09/506,153, filed on Feb. 17, 2000, now abandoned.

(51) Int. Cl.
*C12N 9/12* (2006.01)

(52) U.S. Cl.
USPC ........... 435/194; 435/183; 435/193; 435/195; 530/350

(58) Field of Classification Search
USPC ............... 435/194, 183, 91.1; 536/23.1, 23.2, 536/23.4
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91.2 |
| 4,800,159 A | 1/1989 | Mullis et al. | 435/91.2 |
| 4,889,818 A | 12/1989 | Gelfand et al. | 435/194 |
| 4,965,188 A | 10/1990 | Mullis et al. | 435/6 |
| 5,023,171 A | 6/1991 | Ho et al. | 435/6 |
| 5,066,584 A | 11/1991 | Gyllensten et al. | 435/91.2 |
| 5,075,216 A | 12/1991 | Innes et al. | 435/6 |
| 5,079,352 A | 1/1992 | Gelfand et al. | 536/23.2 |
| 5,091,310 A | 2/1992 | Innes | 435/91.2 |
| 5,104,792 A | 4/1992 | Silver et al. | 435/6 |
| 5,210,036 A | 5/1993 | Comb et al. | |
| 5,242,818 A | 9/1993 | Oshima et al. | |
| 5,436,149 A | 7/1995 | Barnes | 435/194 |
| 5,491,086 A | 2/1996 | Gelfand et al. | 435/194 |
| 5,602,011 A | 2/1997 | Luhm et al. | 435/91.2 |
| 6,008,025 A | 12/1999 | Komatsubara et al. | |
| 6,228,628 B1 * | 5/2001 | Gelfand et al. | 435/194 |
| 6,555,357 B1 * | 4/2003 | Kaiser et al. | 435/252.3 |
| 6,607,883 B1 * | 8/2003 | Frey et al. | 435/6 |
| 6,627,424 B1 * | 9/2003 | Wang | 435/194 |
| 7,425,423 B1 | 9/2008 | Ankenbauer et al. | |
| 2003/0228616 A1 | 12/2003 | Arezi et al. | |
| 2004/0053279 A1 | 3/2004 | Decker et al. | |

FOREIGN PATENT DOCUMENTS

| | | | | |
|---|---|---|---|---|
| EP | 0 712 927 A2 | 5/1996 | ............... | C12N 9/12 |
| EP | 0 745 675 A2 | 12/1996 | | |
| EP | 0 834 570 A1 | 4/1998 | | |
| EP | 0 892 058 A2 | 1/1999 | | |
| GB | 2 344 591 A | 6/2000 | | |
| JP | 19970252776 | 9/1997 | | |
| WO | WO 92/06200 | 4/1992 | | |
| WO | WO 96/10640 A1 | 4/1996 | ............. | C12N 15/54 |
| WO | WO 97/29209 | 8/1997 | | |
| WO | WO 98/14590 | 4/1998 | | |
| WO | WO 98/49274 A1 | 11/1998 | | |
| WO | WO 99/47649 | 9/1999 | | |
| WO | WO 01/18213 | 3/2001 | | |
| WO | WO 01/61015 A2 | 8/2001 | | |
| WO | WO 02/29106 A2 | 4/2002 | ............... | C12N 9/00 |

OTHER PUBLICATIONS

Kawarabayasi et al., EMBL Data library Accession No. C75023, Dec. 15, 1998.*
Pisanii et al. , EMBL Data library Accession No. S23019, Jan. 13, 1995.*
Barnes, *PNAS USA* 91:2216-2220 (1994).
Bernard et al., *Cell* 59:219 (1989).
Eom et al., *Nature* 382: 278-281 (1996).
Flaman et al. *N.A.R.* 22:3259-3260 (1994).
Jacobson et al., *Eur. J. Biochem.* 45:623 (1974).
Joyce and Grindley, *PNAS USA* 80:1830 (1983).
Joyce and Steitz, *Annu. Rev. Biochem.* 63:777-822 (1994).
Kiefer et al., *Structure* 5: 95-108 (1997).
Klenow and Henningsen, *PNAS USA* 65:168 (1970).
Longley et al. *N.A.R.* 18:7317-7322 (1990).
Lawyer et al., *J. Biol. Chem.* 264:6427-6437 (1989).
Mendelman et al., *J. Biol. Chem.* 265(4):2338-2346 (1990).
Park et al., *Mol. Cells* 7(3):419-424 (1997).
Petruska et al., *PNAS USA* 85:6252-6256 (1988).
Akhmetzjanov et al., *Nucleic Acids Research*, 20:5839 (1992).
Asakura et al., *Journal of Fermentation and Bioengineering*, 76:265-269 (1993).
Dabrowski et al., *Protein Expression and Purification*, 14:131-138 (1998).
Datukishvili et al., *Gene*, 177:271-273 (1996).
Edgell et al., *Journal of Bacteriology*, 179:2632-2640 (1997).
Huang et al., *Nucleic Acids Research*, 26:5300-5309 (1998).
Innis et al., *PCR Strategies*, by Academic Press, Inc., Chapter 4—pp. 39-57 (1995).
Jung et al., *Mol. Cells*, 7:769-776 (1997).

(Continued)

*Primary Examiner* — Richard Hutson
(74) *Attorney, Agent, or Firm* — Fanelli Haag & Kilger PLLC

(57) ABSTRACT

Novel thermostable chimeric nucleic acid polymerases and methods for their generation and use are disclosed. It is shown that these chimeric nucleic acid polymerases, such as DNA polymerases, can be constructed using enzymatically active domains, isolated from different proteins or chemically synthesized. It is demonstrated that chimeric nucleic acid polymerases of the present invention possess the chemical and physical properties of their component domains (e.g., exonuclease activity, thermostability) and that the chimeric polymerases are thermostable.

21 Claims, 4 Drawing Sheets

(56) References Cited

OTHER PUBLICATIONS

Kawarabayasi et al., *DNA Research*, 5:55-76 (1998).
Lawyer et al., *J. Biol. Chem.*, 264(11):6427 (1989).
Perler et al., *Pro. Natl. Acad. Sci. USA*, 89:5577-5581 (1992).
Prangishvili et al., *Nucleic Acids Research*, 21:2768 (1993).
Tagaki et al., *Applied and Environmental Microbiology*, 63:4504-4510 (1997).
Uemori et al., *Nucleic Acids Research*, 21:259-265 (1993).
Williams et al., *International Journal of Systematic Bacteriology*, 45:495-499 (1995).
Pisani et al., A DNA polymerase from the archaeon *Sulfolobus solfataricus* shows sequence similarity to family B DNA polymerase, *Nucleic Acids Research*, 20(11): 2711-2716 (1992).
Uemori et al., Organization and nucleotide sequence of the DNA polymerase gene from the archaeon *Pyrococcus furiosus*, *Nucleic Acids Research*, 21(2): 259-265 (1993).
Uemori et al., The Hyperthermophilic Archaeon *Pyrodictium occultum* Has Two α-Like DNA Polymerases, *Journal of Bacteriology*, 177(8): 2164-2177 (1995).
Southworth et al., Cloning of thermostable DNA polymerases from hyperthermophilic marine Archaea with emphasis on *Thermococcus* sp. 9°N-7 and mutations affecting 3'-5' exonuclease activity, *Proc. Natl. Acad. Sci. USA*, 93: 5281-5285 (1996).
Pisani et al., Domain organization and biochemical features of *Sulfolobus solfataricus* DNA polymerase, *Extremophiles*, 2: 171-177 (1998).
Hopfner et al., Crystal structure of a thermostable type B DNA polymerase from *Thermococcus gorgonarius*, *Proc. Natl. Acad. Sci. USA*, 96: 3600-3605 (1999).
Cann et al., Two Family B DNA Polymerases from *Aeropyrum pernix*, an Aerobic Hyperthermophilic Crenarchaeote, *Journal of Bacteriology*, 181(19): 5984-5992 (1999).
Kähler et al., Cloning and Characterization of a Family BDNA Polymerase from the Hyperthermophilic Crenarchaeon *Pyrobaculum islandicum*, *Journal of Bacteriology*, 182(3): 655-663 (2000).
Joyce et al., Function and Structure Relationships in DNA Polymerases, *Annu. Rev. Biochem.*, 63: 777-822 (1994).
Cariello et al., "Fidelity of *Thermococcus litoralis* DNA polymerase (Vent™) in PCR determined by denaturing gradient gel electrophoresis", Nucleic Acids Research, vol. 19 (1991), pp. 4193-4198.
Decker et al., U.S.P.T.O. Office Action, U.S. Appl. No. 10/398,011, Jan. 3, 2007, 19 pgs.
Decker et al., U.S.P.T.O. Office Action, U.S. Appl. No. 10/398,011, Sep. 25, 2007, 12 pgs.
Decker et al., U.S.P.T.O. Office Action, U.S. Appl. No. 10/398,011, Jun. 26, 2008, 9 pgs.
Decker et al., U.S.P.T.O. Office Action, U.S. Appl. No. 10/398,011, Sep. 2, 2009, 10 pgs.
Decker et al., U.S.P.T.O. Office Action, U.S. Appl. No. 10/398,011, Feb. 17, 2010, 15 pgs., Feb. 22, 2011.
Decker et al., U.S.P.T.O. Requirement for Restriction/Election, U.S. Appl. No. 10/398,011, Jan. 24, 2006, 5 pgs.
Y16226, GI:3059149, *Thermococcus gorgonarius* 16S rRNA gene, Apr. 15, 1998.
Y16227, *Thermococcus pacificus* 16S rRNA gene, Apr. 15, 1998.
HGO_A; GI:4699806 , Chain A, Thermostable B Type Dna Polymerase From *Thermococcus*; Jul. 10, 2009.
Hopfner et al., "Crystal structure of a thermostable type B DNA polymerase from *Thermococcus gorgonarius*", Proc. Natl. Acad. Sci. USA, vol. 96 (1999), pp. 3600-3605.
Keohavong et al., "Predominant mutations induced by the *Thermococcus litoralis*, vent DNA polymerase during DNA amplification in vitro." Genome Research, vol. 2 (1993), pp. 288-292.
Kong et al., "Characterization of a DNA Polymerase from the Hyperthermophile Archaea *Thermococcus litoralis*", The Journal of Biological Chemistry, vol. 268 (1993), pp. 1965-1975.
Matilla et al., "Fidelity of DNA synthesis by the *Thermococcus litoralis* DNA polymerase—an extremely heat stable enzyme with proofreading activity", Nucleic Acids Research, vol. 19 (1991), pp. 4967-4973.
Miroshnichenko et al., "*Thermococcus gorgonarius* sp. nov. and *Thermococcus pacificus* sp. nov.: heterotrophic extremely thermophilic archaea from New Zealand submarine hot vents", International Journal of Systematic Bacteriology, vol. 48 (1998), pp. 23-29.
Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.
Ogata and Miura, "Creation of genetic information by DNA polymerase of the archaeon *Thermococcus litoralis*: influences of temperature and ionic strength", Nucleic Acids Research, vol. 26 (1998), pp. 4652-4656.
Ogata and Miura, "Genetic information 'created' by archaebacterial DNA polymerase", Biochem. J., vol. 324 (1997), pp. 667-671.
Decker et al., U.S.P.T.O Office Action, U.S. Appl. No. 10/398,011, Jun. 21, 2011, 12 pgs.
Decker et al., Notice of Allowance, U.S. Appl. No. 10/398,011, Nov. 23, 2011, 7 pgs.

\* cited by examiner

SEQUENCE LISTING

<160> NUMBER OF SEQ ID NOS: 17

<210> SEQ ID NO 1
<211> LENGTH: 552
<212> TYPE: PRT
<213> ORGANISM: Thermus aquaticus

<400> SEQUENCE: 1

```
Leu Leu His Glu Phe Gly Leu Leu Glu Ser Pro Lys Ala Leu Glu Glu
1               5                   10                  15

Ala Pro Trp Pro Pro Glu Gly Ala Phe Val Gly Phe Val Leu Ser
                20                  25                  30

Arg Lys Glu Pro Met Trp Ala Asp Leu Leu Ala Leu Ala Ala Ala Arg
            35                  40                  45

Gly Gly Arg Val His Arg Ala Pro Glu Pro Tyr Lys Ala Leu Arg Asp
        50                  55                  60

Leu Lys Glu Ala Arg Gly Leu Leu Ala Lys Asp Leu Ser Val Leu Ala
65                  70                  75                  80

Leu Arg Glu Gly Leu Gly Leu Pro Pro Gly Asp Asp Pro Met Leu Leu
                85                  90                  95

Ala Tyr Leu Leu Asp Pro Ser Asn Thr Thr Pro Glu Gly Val Ala Arg
                100                 105                 110

Arg Tyr Gly Gly Glu Trp Thr Glu Glu Ala Gly Glu Arg Ala Ala Leu
            115                 120                 125

Ser Glu Arg Leu Phe Ala Asn Leu Trp Gly Arg Leu Glu Gly Glu Glu
        130                 135                 140

Arg Leu Leu Trp Leu Tyr Arg Glu Val Glu Arg Pro Leu Ser Ala Val
145                 150                 155                 160

Leu Ala His Met Glu Ala Thr Gly Val Arg Leu Asp Val Ala Tyr Leu
                165                 170                 175

Arg Ala Leu Ser Leu Glu Val Ala Glu Glu Ile Ala Arg Leu Glu Ala
                180                 185                 190

Glu Val Phe Arg Leu Ala Gly His Pro Phe Asn Leu Asn Ser Arg Asp
            195                 200                 205

Gln Leu Glu Arg Val Leu Phe Asp Glu Leu Gly Leu Pro Ala Ile Gly
        210                 215                 220

Lys Thr Glu Lys Thr Gly Lys Arg Ser Thr Ser Ala Ala Val Leu Glu
225                 230                 235                 240

Ala Leu Arg Glu Ala His Pro Ile Val Glu Lys Ile Leu Gln Tyr Arg
                245                 250                 255
```

```
Glu Leu Thr Lys Leu Lys Ser Thr Tyr Ile Asp Pro Leu Pro Asp Leu
            260                 265                 270

Ile His Pro Arg Thr Gly Arg Leu His Thr Arg Phe Asn Gln Thr Ala
        275                 280                 285

Thr Ala Thr Gly Arg Leu Ser Ser Ser Asp Pro Asn Leu Gln Asn Ile
    290                 295                 300

Pro Val Arg Thr Pro Leu Gly Gln Arg Ile Arg Arg Ala Phe Ile Ala
305                 310                 315                 320

Glu Glu Gly Trp Leu Leu Val Ala Leu Asp Tyr Ser Gln Ile Glu Leu
                325                 330                 335

Arg Val Leu Ala His Leu Ser Gly Asp Glu Asn Leu Ile Arg Val Phe
            340                 345                 350

Gln Glu Gly Arg Asp Ile His Thr Glu Thr Ala Ser Trp Met Phe Gly
        355                 360                 365

Val Pro Arg Glu Ala Val Asp Pro Leu Met Arg Arg Ala Ala Lys Thr
    370                 375                 380

Ile Asn Phe Gly Val Leu Tyr Gly Met Ser Ala His Arg Leu Ser Gln
385                 390                 395                 400

Glu Leu Ala Ile Pro Tyr Glu Glu Ala Gln Ala Phe Ile Glu Arg Tyr
                405                 410                 415

Phe Gln Ser Phe Pro Lys Val Arg Ala Trp Ile Glu Lys Thr Leu Glu
            420                 425                 430

Glu Gly Arg Arg Arg Gly Tyr Val Glu Thr Leu Phe Gly Arg Arg Arg
        435                 440                 445

Tyr Val Pro Asp Leu Glu Ala Arg Val Lys Ser Val Arg Glu Ala Ala
    450                 455                 460

Glu Arg Met Ala Phe Asn Met Pro Val Gln Gly Thr Ala Ala Asp Leu
465                 470                 475                 480

Met Lys Leu Ala Met Val Lys Leu Phe Pro Arg Leu Glu Glu Met Gly
                485                 490                 495

Ala Arg Met Leu Leu Gln Val His Asp Glu Leu Val Leu Glu Ala Pro
            500                 505                 510

Lys Glu Arg Ala Glu Ala Val Ala Arg Leu Ala Lys Glu Val Met Glu
        515                 520                 525

Gly Val Tyr Pro Leu Ala Val Pro Leu Glu Val Glu Val Gly Ile Gly
    530                 535                 540

Glu Asp Trp Leu Ser Ala Lys Glu
545                 550

<210> SEQ ID NO 2
<211> LENGTH: 562
<212> TYPE: PRT
<213> ORGANISM: Thermus thermophilus

<400> SEQUENCE: 2

Ala Phe Leu Glu Arg Leu Glu Phe Gly Ser Leu Leu His Glu Phe Gly
1               5                   10                  15

Leu Leu Glu Ala Pro Ala Pro Leu Glu Glu Ala Pro Trp Pro Pro Pro
            20                  25                  30

Glu Gly Ala Phe Val Gly Phe Val Leu Ser Arg Pro Glu Pro Met Trp
        35                  40                  45

Ala Glu Leu Lys Ala Leu Ala Ala Cys Arg Asp Gly Arg Val His Arg
    50                  55                  60

Ala Ala Asp Pro Leu Ala Gly Leu Lys Asp Leu Lys Glu Val Arg Gly
65                  70                  75                  80
```

-continued

```
Leu Leu Ala Lys Asp Leu Ala Val Leu Ala Ser Arg Glu Gly Leu Asp
                85                  90                  95
Leu Val Pro Gly Asp Asp Pro Met Leu Ala Tyr Leu Leu Asp Pro
            100                 105                 110
Ser Asn Thr Thr Pro Glu Gly Val Ala Arg Arg Tyr Gly Gly Glu Trp
        115                 120                 125
Thr Glu Asp Ala Ala His Arg Ala Leu Leu Ser Glu Arg Leu His Arg
    130                 135                 140
Asn Leu Leu Lys Arg Leu Glu Gly Glu Lys Leu Leu Trp Leu Tyr
145                 150                 155                 160
His Glu Val Glu Lys Pro Leu Ser Arg Val Leu Ala His Met Glu Ala
                165                 170                 175
Thr Gly Val Arg Arg Asp Val Ala Tyr Leu Gln Ala Leu Ser Leu Glu
            180                 185                 190
Leu Ala Glu Glu Ile Arg Arg Leu Glu Glu Val Phe Arg Leu Ala
        195                 200                 205
Gly His Pro Phe Asn Leu Asn Ser Arg Asp Gln Leu Glu Arg Val Leu
    210                 215                 220
Phe Asp Glu Leu Arg Leu Pro Ala Leu Gly Lys Thr Gln Lys Thr Gly
225                 230                 235                 240
Lys Arg Ser Thr Ser Ala Ala Val Leu Glu Ala Leu Arg Glu Ala His
                245                 250                 255
Pro Ile Val Glu Lys Ile Leu Gln His Arg Glu Leu Thr Lys Leu Lys
            260                 265                 270
Asn Thr Tyr Val Asp Pro Leu Pro Ser Leu Val His Pro Arg Thr Gly
        275                 280                 285
Arg Leu His Thr Arg Phe Asn Gln Thr Ala Thr Ala Thr Gly Arg Leu
    290                 295                 300
Ser Ser Ser Asp Pro Asn Leu Gln Asn Ile Pro Val Arg Thr Pro Leu
305                 310                 315                 320
Gly Gln Arg Ile Arg Arg Ala Phe Val Ala Glu Ala Gly Trp Ala Leu
                325                 330                 335
Val Ala Leu Asp Tyr Ser Gln Ile Glu Leu Arg Val Leu Ala His Leu
            340                 345                 350
Ser Gly Asp Glu Asn Leu Ile Arg Val Phe Gln Glu Gly Lys Asp Ile
        355                 360                 365
His Thr Gln Thr Ala Ser Trp Met Phe Gly Val Pro Pro Glu Ala Val
    370                 375                 380
Asp Pro Leu Met Arg Arg Ala Ala Lys Thr Val Asn Phe Gly Val Leu
385                 390                 395                 400
Tyr Gly Met Ser Ala His Arg Leu Ser Gln Glu Leu Ala Ile Pro Tyr
                405                 410                 415
Glu Glu Ala Val Ala Phe Ile Glu Arg Tyr Phe Gln Ser Phe Pro Lys
            420                 425                 430
Val Arg Ala Trp Ile Glu Lys Thr Leu Glu Glu Gly Arg Lys Arg Gly
        435                 440                 445
Tyr Val Glu Thr Leu Phe Gly Arg Arg Tyr Val Pro Asp Leu Asn
    450                 455                 460
Ala Arg Val Lys Ser Val Arg Glu Ala Ala Glu Arg Met Ala Phe Asn
465                 470                 475                 480
Met Pro Val Gln Gly Thr Ala Ala Asp Leu Met Lys Leu Ala Met Val
                485                 490                 495
Lys Leu Phe Pro Arg Leu Arg Glu Met Gly Ala Arg Met Leu Leu Gln
            500                 505                 510
```

-continued

Val His Asp Glu Leu Leu Leu Glu Ala Pro Gln Ala Arg Ala Glu Glu
    515                 520                 525

Val Ala Ala Leu Ala Lys Glu Ala Met Glu Lys Ala Tyr Pro Leu Ala
    530                 535                 540

Val Pro Leu Glu Val Glu Val Gly Met Gly Glu Asp Trp Leu Ser Ala
545                 550                 555                 560

Lys Gly

<210> SEQ ID NO 3
<211> LENGTH: 396
<212> TYPE: PRT
<213> ORGANISM: Pyrococcus horikoshii

<400> SEQUENCE: 3

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Arg Asp Asp Ser Ala Ile
        35                  40                  45

Asp Glu Ile Lys Lys Ile Thr Ala Gln Arg His Gly Lys Val Val Arg
    50                  55                  60

Ile Val Glu Thr Glu Lys Ile Gln Arg Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Asp Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Lys Leu Thr Phe Leu Ala Val Asp Ile Glu Thr
    130                 135                 140

Leu Tyr His Glu Gly Glu Glu Phe Gly Lys Gly Pro Val Ile Met Ile
145                 150                 155                 160

Ser Tyr Ala Asp Glu Glu Gly Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Leu Ile Arg Val Ile Lys Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Leu Leu Gly Arg Asp Asn Ser Glu Pro Lys
225                 230                 235                 240

Met Gln Lys Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Val Thr Tyr
305                 310                 315                 320

```
Glu Leu Gly Arg Glu Phe Pro Met Glu Ala Gln Leu Ala Arg Leu
                325                 330                 335

Val Gly Gln Pro Val Trp Asp Val Ser Arg Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Tyr Glu Arg Arg Leu Arg Glu Ser
    370                 375                 380

Tyr Glu Gly Gly Tyr Val Lys Glu Pro Glu Lys Gly
385                 390                 395

<210> SEQ ID NO 4
<211> LENGTH: 396
<212> TYPE: PRT
<213> ORGANISM: Pyrococcus woesei

<400> SEQUENCE: 4

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300
```

```
Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
            325                 330                 335

Val Gly Gln Pro Leu Trp Asp Val Ser Arg Ser Ser Thr Gly Asn Leu
        340                 345                 350

Val Glu Trp Phe Leu Leu Arg Lys Ala Tyr Glu Arg Asn Glu Val Ala
    355                 360                 365

Pro Asn Lys Pro Ser Glu Glu Tyr Gln Arg Arg Leu Arg Glu Ser
370                 375                 380

Tyr Thr Gly Gly Phe Val Lys Glu Pro Glu Lys Gly
385                 390                 395

<210> SEQ ID NO 5
<211> LENGTH: 421
<212> TYPE: PRT
<213> ORGANISM: Pyrococcus woesei

<400> SEQUENCE: 5

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285
```

```
Lys Val Tyr Ala Asp Glu Ile Ala Lys Ala Trp Glu Ser Gly Glu Asn
            290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Leu Arg Glu Ser
370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Thr
                405                 410                 415

His Asn Val Ser Pro
            420

<210> SEQ ID NO 6
<211> LENGTH: 508
<212> TYPE: PRT
<213> ORGANISM: Sulfolobus solfataricus

<400> SEQUENCE: 6

Met Thr Lys Gln Leu Thr Leu Phe Asp Ile Pro Ser Ser Lys Pro Ala
1               5                   10                  15

Lys Ser Glu Gln Asn Thr Gln Gln Ser Gln Gln Ser Ala Pro Val Glu
            20                  25                  30

Glu Lys Lys Val Val Arg Arg Glu Trp Leu Glu Glu Ala Gln Glu Asn
        35                  40                  45

Lys Ile Tyr Phe Leu Leu Gln Val Asp Tyr Asp Gly Lys Gly Lys
    50                  55                  60

Ala Val Cys Lys Leu Phe Asp Lys Glu Thr Gln Lys Ile Tyr Ala Leu
65                  70                  75                  80

Tyr Asp Asn Thr Gly His Lys Pro Tyr Phe Leu Val Asp Leu Glu Pro
                85                  90                  95

Asp Lys Val Gly Lys Ile Pro Lys Ile Val Arg Asp Pro Ser Phe Asp
            100                 105                 110

His Ile Glu Thr Val Ser Lys Ile Asp Pro Tyr Thr Trp Asn Lys Phe
        115                 120                 125

Lys Leu Thr Lys Ile Val Val Arg Asp Pro His Ala Val Arg Arg Leu
    130                 135                 140

Arg Asn Asp Val Pro Lys Ala Tyr Glu Ala His Ile Lys Tyr Phe Asn
145                 150                 155                 160

Asn Tyr Met Tyr Asp Ile Gly Leu Ile Pro Gly Met Pro Tyr Val Val
                165                 170                 175

Lys Asn Gly Lys Leu Glu Ser Val Tyr Leu Ser Leu Asp Glu Lys Asp
            180                 185                 190

Val Glu Glu Ile Lys Lys Ala Phe Ala Asp Ser Asp Glu Met Thr Arg
        195                 200                 205

Gln Met Ala Val Asp Trp Leu Pro Ile Phe Glu Thr Glu Ile Pro Lys
    210                 215                 220

Ile Lys Arg Val Ala Ile Asp Ile Glu Val Tyr Thr Pro Val Lys Gly
225                 230                 235                 240
```

```
Arg Ile Pro Asp Ser Gln Lys Ala Glu Phe Pro Ile Ser Ile Ala
            245                 250                 255
Leu Ala Gly Ser Asp Gly Leu Lys Lys Val Leu Val Leu Asn Arg Asn
        260                 265                 270
Asp Val Asn Glu Gly Ser Val Lys Leu Asp Gly Ile Ser Val Glu Arg
            275                 280                 285
Phe Asn Thr Glu Tyr Glu Leu Leu Gly Arg Phe Phe Asp Ile Leu Leu
        290                 295                 300
Glu Tyr Pro Ile Val Leu Thr Phe Asn Gly Asp Asp Phe Asp Leu Pro
305                 310                 315                 320
Tyr Ile Tyr Phe Arg Ala Leu Lys Leu Gly Tyr Phe Pro Glu Glu Ile
                325                 330                 335
Pro Ile Asp Val Ala Gly Lys Asp Glu Ala Lys Tyr Leu Ala Gly Leu
            340                 345                 350
His Ile Asp Leu Tyr Lys Phe Phe Asn Lys Ala Val Arg Asn Tyr
        355                 360                 365
Ala Phe Glu Gly Lys Tyr Asn Glu Tyr Asn Leu Asp Ala Val Ala Lys
        370                 375                 380
Ala Leu Leu Gly Thr Ser Lys Val Lys Val Asp Thr Leu Ile Ser Phe
385                 390                 395                 400
Leu Asp Val Glu Lys Leu Ile Glu Tyr Asn Phe Arg Asp Ala Glu Ile
            405                 410                 415
Thr Leu Gln Leu Thr Thr Phe Asn Asn Asp Leu Thr Met Lys Leu Ile
        420                 425                 430
Val Leu Phe Ser Arg Ile Ser Arg Leu Gly Ile Glu Leu Thr Arg
        435                 440                 445
Thr Glu Ile Ser Thr Trp Val Lys Asn Leu Tyr Tyr Trp Glu His Arg
450                 455                 460
Lys Arg Asn Trp Leu Ile Pro Leu Lys Glu Glu Ile Leu Ala Lys Ser
465                 470                 475                 480
Ser Asn Ile Arg Thr Ser Ala Leu Ile Lys Gly Lys Gly Tyr Lys Gly
            485                 490                 495
Ala Val Val Ile Asp Pro Pro Ala Gly Ile Phe Phe
                500                 505

<210> SEQ ID NO 7
<211> LENGTH: 562
<212> TYPE: PRT
<213> ORGANISM: Thermus aquaticus

<400> SEQUENCE: 7

Ala Phe Leu Glu Arg Leu Glu Phe Gly Ser Leu Leu His Glu Phe Gly
1               5                   10                  15
Leu Leu Glu Ser Pro Lys Ala Leu Glu Glu Ala Pro Trp Pro Pro
            20                  25                  30
Glu Gly Ala Phe Val Gly Phe Val Leu Ser Arg Lys Glu Pro Met Trp
        35                  40                  45
Ala Asp Leu Leu Ala Leu Ala Ala Ala Arg Gly Gly Arg Val His Arg
    50                  55                  60
Ala Pro Glu Pro Tyr Lys Ala Leu Arg Asp Leu Lys Glu Ala Arg Gly
65                  70                  75                  80
Leu Leu Ala Lys Asp Leu Ser Val Leu Ala Leu Arg Glu Gly Leu Gly
                85                  90                  95
Leu Pro Pro Gly Asp Asp Pro Met Leu Leu Ala Tyr Leu Leu Asp Pro
            100                 105                 110
```

-continued

```
Ser Asn Thr Thr Pro Glu Gly Val Ala Arg Arg Tyr Gly Gly Glu Trp
        115                 120                 125

Thr Glu Glu Ala Gly Glu Arg Ala Ala Leu Ser Glu Arg Leu Phe Ala
    130                 135                 140

Asn Leu Trp Gly Arg Leu Glu Gly Glu Arg Leu Leu Trp Leu Tyr
145                 150                 155                 160

Arg Glu Val Glu Arg Pro Leu Ser Ala Val Leu Ala His Met Glu Ala
                165                 170                 175

Thr Gly Val Arg Leu Asp Val Ala Tyr Leu Arg Ala Leu Ser Leu Glu
            180                 185                 190

Val Ala Glu Glu Ile Ala Arg Leu Glu Ala Glu Val Phe Arg Leu Ala
        195                 200                 205

Gly His Pro Phe Asn Leu Asn Ser Arg Asp Gln Leu Glu Arg Val Leu
    210                 215                 220

Phe Asp Glu Leu Gly Leu Pro Ala Ile Gly Lys Thr Glu Lys Thr Gly
225                 230                 235                 240

Lys Arg Ser Thr Ser Ala Ala Val Leu Glu Ala Leu Arg Glu Ala His
                245                 250                 255

Pro Ile Val Glu Lys Ile Leu Gln Tyr Arg Glu Leu Thr Lys Leu Lys
            260                 265                 270

Ser Thr Tyr Ile Asp Pro Leu Pro Asp Leu Ile His Pro Arg Thr Gly
        275                 280                 285

Arg Leu His Thr Arg Phe Asn Gln Thr Ala Thr Ala Thr Gly Arg Leu
    290                 295                 300

Ser Ser Ser Asp Pro Asn Leu Gln Asn Ile Pro Val Arg Thr Pro Leu
305                 310                 315                 320

Gly Gln Arg Ile Arg Arg Ala Phe Ile Ala Glu Glu Gly Trp Leu Leu
                325                 330                 335

Val Ala Leu Asp Tyr Ser Gln Ile Glu Leu Arg Val Leu Ala His Leu
            340                 345                 350

Ser Gly Asp Glu Asn Leu Ile Arg Val Phe Gln Glu Gly Arg Asp Ile
        355                 360                 365

His Thr Glu Thr Ala Ser Trp Met Phe Gly Val Pro Arg Glu Ala Val
    370                 375                 380

Asp Pro Leu Met Arg Arg Ala Ala Lys Thr Ile Asn Phe Gly Val Leu
385                 390                 395                 400

Tyr Gly Met Ser Ala His Arg Leu Ser Gln Glu Leu Ala Ile Pro Tyr
                405                 410                 415

Glu Glu Ala Gln Ala Phe Ile Glu Arg Tyr Phe Gln Ser Phe Pro Lys
            420                 425                 430

Val Arg Ala Trp Ile Glu Lys Thr Leu Glu Glu Gly Arg Arg Arg Gly
        435                 440                 445

Tyr Val Glu Thr Leu Phe Gly Arg Arg Arg Tyr Val Pro Asp Leu Glu
    450                 455                 460

Ala Arg Val Lys Ser Val Arg Glu Ala Ala Glu Arg Met Ala Phe Asn
465                 470                 475                 480

Met Pro Val Gln Gly Thr Ala Ala Asp Leu Met Lys Leu Ala Met Val
                485                 490                 495

Lys Leu Phe Pro Arg Leu Glu Glu Met Gly Ala Arg Met Leu Leu Gln
            500                 505                 510

Val His Asp Glu Leu Val Leu Glu Ala Pro Lys Glu Arg Ala Glu Ala
        515                 520                 525

Val Ala Arg Leu Ala Lys Glu Val Met Glu Gly Val Tyr Pro Leu Ala
    530                 535                 540
```

Val Pro Leu Glu Val Glu Val Gly Ile Gly Glu Asp Trp Leu Ser Ala
545                 550                 555                 560

Lys Glu

<210> SEQ ID NO 8
<211> LENGTH: 958
<212> TYPE: PRT
<213> ORGANISM: Artificial Sequence
<220> FEATURE:
<223> OTHER INFORMATION: Description of Artificial Sequence: Pho/Taq
      Chimeric polymerase

<400> SEQUENCE: 8

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Arg Asp Asp Ser Ala Ile
            35                  40                  45

Asp Glu Ile Lys Lys Ile Thr Ala Gln Arg His Gly Lys Val Val Arg
    50                  55                  60

Ile Val Glu Thr Glu Lys Ile Gln Arg Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Asp Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Lys Leu Thr Phe Leu Ala Val Asp Ile Glu Thr
    130                 135                 140

Leu Tyr His Glu Gly Glu Glu Phe Gly Lys Gly Pro Val Ile Met Ile
145                 150                 155                 160

Ser Tyr Ala Asp Glu Glu Gly Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Leu Ile Arg Val Ile Lys Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Leu Leu Gly Arg Asp Asn Ser Glu Pro Lys
225                 230                 235                 240

Met Gln Lys Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ala Arg Leu
                325                 330                 335

-continued

Val Gly Gln Pro Val Trp Asp Val Ser Arg Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Tyr Glu Arg Arg Leu Arg Glu Ser
        370                 375                 380

Tyr Glu Gly Gly Tyr Val Lys Glu Pro Glu Lys Gly Ala Phe Leu Glu
385                 390                 395                 400

Arg Leu Glu Phe Gly Ser Leu Leu His Glu Phe Gly Leu Leu Glu Ser
                405                 410                 415

Pro Lys Ala Leu Glu Glu Ala Pro Trp Pro Pro Glu Gly Ala Phe
        420                 425                 430

Val Gly Phe Val Leu Ser Arg Lys Glu Pro Met Trp Ala Asp Leu Leu
        435                 440                 445

Ala Leu Ala Ala Ala Arg Gly Gly Arg Val His Arg Ala Pro Glu Pro
        450                 455                 460

Tyr Lys Ala Leu Arg Asp Leu Lys Glu Ala Arg Gly Leu Leu Ala Lys
465                 470                 475                 480

Asp Leu Ser Val Leu Ala Leu Arg Glu Gly Leu Gly Leu Pro Pro Gly
                485                 490                 495

Asp Asp Pro Met Leu Leu Ala Tyr Leu Leu Asp Pro Ser Asn Thr Thr
            500                 505                 510

Pro Glu Gly Val Ala Arg Arg Tyr Gly Gly Glu Trp Thr Glu Glu Ala
        515                 520                 525

Gly Glu Arg Ala Ala Leu Ser Glu Arg Leu Phe Ala Asn Leu Trp Gly
        530                 535                 540

Arg Leu Glu Gly Glu Glu Arg Leu Leu Trp Leu Tyr Arg Glu Val Glu
545                 550                 555                 560

Arg Pro Leu Ser Ala Val Leu Ala His Met Glu Ala Thr Gly Val Arg
                565                 570                 575

Leu Asp Val Ala Tyr Leu Arg Ala Leu Ser Leu Glu Val Ala Glu Glu
            580                 585                 590

Ile Ala Arg Leu Glu Ala Glu Val Phe Arg Leu Ala Gly His Pro Phe
        595                 600                 605

Asn Leu Asn Ser Arg Asp Gln Leu Glu Arg Val Leu Phe Asp Glu Leu
        610                 615                 620

Gly Leu Pro Ala Ile Gly Lys Thr Glu Lys Thr Gly Lys Arg Ser Thr
625                 630                 635                 640

Ser Ala Ala Val Leu Glu Ala Leu Arg Glu Ala His Pro Ile Val Glu
                645                 650                 655

Lys Ile Leu Gln Tyr Arg Glu Leu Thr Lys Leu Lys Ser Thr Tyr Ile
            660                 665                 670

Asp Pro Leu Pro Asp Leu Ile His Pro Arg Thr Gly Arg Leu His Thr
        675                 680                 685

Arg Phe Asn Gln Thr Ala Thr Ala Thr Gly Arg Leu Ser Ser Ser Asp
        690                 695                 700

Pro Asn Leu Gln Asn Ile Pro Val Arg Thr Pro Leu Gly Gln Arg Ile
705                 710                 715                 720

Arg Arg Ala Phe Ile Ala Glu Glu Gly Trp Leu Leu Val Ala Leu Asp
                725                 730                 735

Tyr Ser Gln Ile Glu Leu Arg Val Leu Ala His Leu Ser Gly Asp Glu
            740                 745                 750

Asn Leu Ile Arg Val Phe Gln Glu Gly Arg Asp Ile His Thr Glu Thr
        755                 760                 765

Ala Ser Trp Met Phe Gly Val Pro Arg Glu Ala Val Asp Pro Leu Met
770                 775                 780

Arg Arg Ala Ala Lys Thr Ile Asn Phe Gly Val Leu Tyr Gly Met Ser
785                 790                 795                 800

Ala His Arg Leu Ser Gln Glu Leu Ala Ile Pro Tyr Glu Glu Ala Gln
            805                 810                 815

Ala Phe Ile Glu Arg Tyr Phe Gln Ser Phe Pro Lys Val Arg Ala Trp
            820                 825                 830

Ile Glu Lys Thr Leu Glu Glu Gly Arg Arg Arg Gly Tyr Val Glu Thr
            835                 840                 845

Leu Phe Gly Arg Arg Arg Tyr Val Pro Asp Leu Glu Ala Arg Val Lys
        850                 855                 860

Ser Val Arg Glu Ala Ala Glu Arg Met Ala Phe Asn Met Pro Val Gln
865                 870                 875                 880

Gly Thr Ala Ala Asp Leu Met Lys Leu Ala Met Val Lys Leu Phe Pro
            885                 890                 895

Arg Leu Glu Glu Met Gly Ala Arg Met Leu Leu Gln Val His Asp Glu
            900                 905                 910

Leu Val Leu Glu Ala Pro Lys Glu Arg Ala Glu Ala Val Ala Arg Leu
            915                 920                 925

Ala Lys Glu Val Met Glu Gly Val Tyr Pro Leu Ala Val Pro Leu Glu
            930                 935                 940

Val Glu Val Gly Ile Gly Glu Asp Trp Leu Ser Ala Lys Glu
945                 950                 955

<210> SEQ ID NO 9
<211> LENGTH: 958
<212> TYPE: PRT
<213> ORGANISM: Artificial Sequence
<220> FEATURE:
<223> OTHER INFORMATION: Description of Artificial Sequence: Pwo/Taq
      Chimeric polymerase

<400> SEQUENCE: 9

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

```
Asp Leu Pro Tyr Val Glu Val Ser Ser Glu Arg Glu Met Ile Lys
            180                 185                 190
Arg Phe Leu Arg Ile Ile Arg Glu Lys Asp Pro Asp Ile Ile Val Thr
        195                 200                 205
Tyr Asn Gly Asp Ser Phe Asp Phe Pro Tyr Leu Ala Lys Arg Ala Glu
    210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
            245                 250                 255
His Phe Asp Leu Tyr His Val Ile Thr Arg Thr Ile Asn Leu Pro Thr
        260                 265                 270
Tyr Thr Leu Glu Ala Val Tyr Glu Ala Ile Phe Gly Lys Pro Lys Glu
    275                 280                 285
Lys Val Tyr Ala Asp Glu Ile Ala Lys Ala Trp Glu Ser Gly Glu Asn
290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
            325                 330                 335
Val Gly Gln Pro Leu Trp Asp Val Ser Arg Ser Ser Thr Gly Asn Leu
        340                 345                 350
Val Glu Trp Phe Leu Leu Arg Lys Ala Tyr Glu Arg Asn Glu Val Ala
    355                 360                 365
Pro Asn Lys Pro Ser Glu Glu Tyr Gln Arg Arg Leu Arg Glu Ser
370                 375                 380
Tyr Thr Gly Gly Phe Val Lys Glu Pro Glu Lys Gly Ala Phe Leu Glu
385                 390                 395                 400
Arg Leu Glu Phe Gly Ser Leu Leu His Glu Phe Gly Leu Leu Glu Ser
            405                 410                 415
Pro Lys Ala Leu Glu Glu Ala Pro Trp Pro Pro Glu Gly Ala Phe
        420                 425                 430
Val Gly Phe Val Leu Ser Arg Lys Glu Pro Met Trp Ala Asp Leu Leu
    435                 440                 445
Ala Leu Ala Ala Ala Arg Gly Gly Arg Val His Arg Ala Pro Glu Pro
450                 455                 460
Tyr Lys Ala Leu Arg Asp Leu Lys Glu Ala Arg Gly Leu Leu Ala Lys
465                 470                 475                 480
Asp Leu Ser Val Leu Ala Leu Arg Glu Gly Leu Gly Leu Pro Pro Gly
            485                 490                 495
Asp Asp Pro Met Leu Leu Ala Tyr Leu Leu Asp Pro Ser Asn Thr Thr
        500                 505                 510
Pro Glu Gly Val Ala Arg Arg Tyr Gly Gly Glu Trp Thr Glu Glu Ala
    515                 520                 525
Gly Glu Arg Ala Ala Leu Ser Glu Arg Leu Phe Ala Asn Leu Trp Gly
530                 535                 540
Arg Leu Glu Gly Glu Glu Arg Leu Leu Trp Leu Tyr Arg Glu Val Glu
545                 550                 555                 560
Arg Pro Leu Ser Ala Val Leu Ala His Met Glu Ala Thr Gly Val Arg
            565                 570                 575
Leu Asp Val Ala Tyr Leu Arg Ala Leu Ser Leu Glu Val Ala Glu Glu
        580                 585                 590
Ile Ala Arg Leu Glu Ala Glu Val Phe Arg Leu Ala Gly His Pro Phe
```

```
                595                 600                 605
Asn Leu Asn Ser Arg Asp Gln Leu Glu Arg Val Leu Phe Asp Glu Leu
            610                 615                 620
Gly Leu Pro Ala Ile Gly Lys Thr Glu Lys Thr Gly Lys Arg Ser Thr
625                 630                 635                 640
Ser Ala Ala Val Leu Glu Ala Leu Arg Glu Ala His Pro Ile Val Glu
                645                 650                 655
Lys Ile Leu Gln Tyr Arg Glu Leu Thr Lys Leu Lys Ser Thr Tyr Ile
            660                 665                 670
Asp Pro Leu Pro Asp Leu Ile His Pro Arg Thr Gly Arg Leu His Thr
        675                 680                 685
Arg Phe Asn Gln Thr Ala Thr Ala Thr Gly Arg Leu Ser Ser Ser Asp
    690                 695                 700
Pro Asn Leu Gln Asn Ile Pro Val Arg Thr Pro Leu Gly Gln Arg Ile
705                 710                 715                 720
Arg Arg Ala Phe Ile Ala Glu Glu Gly Trp Leu Leu Val Ala Leu Asp
                725                 730                 735
Tyr Ser Gln Ile Glu Leu Arg Val Leu Ala His Leu Ser Gly Asp Glu
            740                 745                 750
Asn Leu Ile Arg Val Phe Gln Glu Gly Arg Asp Ile His Thr Glu Thr
        755                 760                 765
Ala Ser Trp Met Phe Gly Val Pro Arg Glu Ala Val Asp Pro Leu Met
    770                 775                 780
Arg Arg Ala Ala Lys Thr Ile Asn Phe Gly Val Leu Tyr Gly Met Ser
785                 790                 795                 800
Ala His Arg Leu Ser Gln Glu Leu Ala Ile Pro Tyr Glu Glu Ala Gln
                805                 810                 815
Ala Phe Ile Glu Arg Tyr Phe Gln Ser Phe Pro Lys Val Arg Ala Trp
            820                 825                 830
Ile Glu Lys Thr Leu Glu Glu Gly Arg Arg Arg Gly Tyr Val Glu Thr
        835                 840                 845
Leu Phe Gly Arg Arg Arg Tyr Val Pro Asp Leu Glu Ala Arg Val Lys
    850                 855                 860
Ser Val Arg Glu Ala Ala Glu Arg Met Ala Phe Asn Met Pro Val Gln
865                 870                 875                 880
Gly Thr Ala Ala Asp Leu Met Lys Leu Ala Met Val Lys Leu Phe Pro
                885                 890                 895
Arg Leu Glu Glu Met Gly Ala Arg Met Leu Leu Gln Val His Asp Glu
            900                 905                 910
Leu Val Leu Glu Ala Pro Lys Glu Arg Ala Glu Ala Val Ala Arg Leu
        915                 920                 925
Ala Lys Glu Val Met Glu Gly Val Tyr Pro Leu Ala Val Pro Leu Glu
    930                 935                 940
Val Glu Val Gly Ile Gly Glu Asp Trp Leu Ser Ala Lys Glu
945                 950                 955

<210> SEQ ID NO 10
<211> LENGTH: 1060
<212> TYPE: PRT
<213> ORGANISM: Artificial Sequence
<220> FEATURE:
<223> OTHER INFORMATION: Description of Artificial Sequence: Sso/Taq
      Chimeric polymerase

<400> SEQUENCE: 10

Met Thr Lys Gln Leu Thr Leu Phe Asp Ile Pro Ser Ser Lys Pro Ala
```

-continued

```
1               5                   10                  15
Lys Ser Glu Gln Asn Thr Gln Gln Ser Gln Ser Ala Pro Val Glu
                20                  25                  30

Glu Lys Lys Val Val Arg Arg Glu Trp Leu Glu Glu Ala Gln Glu Asn
                35                  40                  45

Lys Ile Tyr Phe Leu Leu Gln Val Asp Tyr Asp Gly Lys Lys Gly Lys
 50                  55                  60

Ala Val Cys Lys Leu Phe Asp Lys Glu Thr Gln Lys Ile Tyr Ala Leu
 65                  70                  75                  80

Tyr Asp Asn Thr Gly His Lys Pro Tyr Phe Leu Val Asp Leu Glu Pro
                85                  90                  95

Asp Lys Val Gly Lys Ile Pro Lys Ile Val Arg Asp Pro Ser Phe Asp
                100                 105                 110

His Ile Glu Thr Val Ser Lys Ile Asp Pro Tyr Thr Trp Asn Lys Phe
                115                 120                 125

Lys Leu Thr Lys Ile Val Val Arg Asp Pro His Ala Val Arg Arg Leu
                130                 135                 140

Arg Asn Asp Val Pro Lys Ala Tyr Glu Ala His Ile Lys Tyr Phe Asn
145                 150                 155                 160

Asn Tyr Met Tyr Asp Ile Gly Leu Ile Pro Gly Met Pro Tyr Val Val
                165                 170                 175

Lys Asn Gly Lys Leu Glu Ser Val Tyr Leu Ser Leu Asp Glu Lys Asp
                180                 185                 190

Val Glu Glu Ile Lys Lys Ala Phe Ala Asp Ser Asp Glu Met Thr Arg
                195                 200                 205

Gln Met Ala Val Asp Trp Leu Pro Ile Phe Glu Thr Glu Ile Pro Lys
                210                 215                 220

Ile Lys Arg Val Ala Ile Asp Ile Glu Val Tyr Thr Pro Val Lys Gly
225                 230                 235                 240

Arg Ile Pro Asp Ser Gln Lys Ala Glu Phe Pro Ile Ile Ser Ile Ala
                245                 250                 255

Leu Ala Gly Ser Asp Gly Leu Lys Lys Val Leu Val Leu Asn Arg Asn
                260                 265                 270

Asp Val Asn Glu Gly Ser Val Lys Leu Asp Gly Ile Ser Val Glu Arg
                275                 280                 285

Phe Asn Thr Glu Tyr Glu Leu Leu Gly Arg Phe Phe Asp Ile Leu Leu
                290                 295                 300

Glu Tyr Pro Ile Val Leu Thr Phe Asn Gly Asp Asp Phe Asp Leu Pro
305                 310                 315                 320

Tyr Ile Tyr Phe Arg Ala Leu Lys Leu Gly Tyr Phe Pro Glu Glu Ile
                325                 330                 335

Pro Ile Asp Val Ala Gly Lys Asp Glu Ala Lys Tyr Leu Ala Gly Leu
                340                 345                 350

His Ile Asp Leu Tyr Lys Phe Phe Phe Asn Lys Ala Val Arg Asn Tyr
                355                 360                 365

Ala Phe Glu Gly Lys Tyr Asn Glu Tyr Asn Leu Asp Ala Val Ala Lys
 370                 375                 380

Ala Leu Leu Gly Thr Ser Lys Val Lys Val Asp Thr Leu Ile Ser Phe
385                 390                 395                 400

Leu Asp Val Glu Lys Leu Ile Glu Tyr Asn Phe Arg Asp Ala Glu Ile
                405                 410                 415

Thr Leu Gln Leu Thr Thr Phe Asn Asn Asp Leu Thr Met Lys Leu Ile
                420                 425                 430
```

-continued

```
Val Leu Phe Ser Arg Ile Ser Arg Leu Gly Ile Glu Glu Leu Thr Arg
            435                 440                 445
Thr Glu Ile Ser Thr Trp Val Lys Asn Leu Tyr Tyr Trp Glu His Arg
        450                 455                 460
Lys Arg Asn Trp Leu Ile Pro Leu Lys Glu Glu Ile Leu Ala Lys Ser
465                 470                 475                 480
Ser Asn Ile Arg Thr Ser Ala Leu Ile Lys Gly Lys Gly Tyr Lys Gly
                485                 490                 495
Ala Val Val Ile Asp Pro Pro Ala Gly Ile Phe Phe Leu Leu His Glu
            500                 505                 510
Phe Gly Leu Leu Glu Ser Pro Lys Ala Leu Glu Ala Pro Trp Pro
        515                 520                 525
Pro Pro Glu Gly Ala Phe Val Gly Phe Val Leu Ser Arg Lys Glu Pro
    530                 535                 540
Met Trp Ala Asp Leu Leu Ala Leu Ala Ala Arg Gly Gly Arg Val
545                 550                 555                 560
His Arg Ala Pro Glu Pro Tyr Lys Ala Leu Arg Asp Leu Lys Glu Ala
                565                 570                 575
Arg Gly Leu Leu Ala Lys Asp Leu Ser Val Leu Ala Leu Arg Glu Gly
            580                 585                 590
Leu Gly Leu Pro Pro Gly Asp Pro Met Leu Leu Ala Tyr Leu Leu
        595                 600                 605
Asp Pro Ser Asn Thr Thr Pro Glu Gly Val Ala Arg Arg Tyr Gly Gly
    610                 615                 620
Glu Trp Thr Glu Glu Ala Gly Glu Arg Ala Ala Leu Ser Glu Arg Leu
625                 630                 635                 640
Phe Ala Asn Leu Trp Gly Arg Leu Glu Gly Glu Glu Arg Leu Leu Trp
                645                 650                 655
Leu Tyr Arg Glu Val Glu Arg Pro Leu Ser Ala Val Leu Ala His Met
            660                 665                 670
Glu Ala Thr Gly Val Arg Leu Asp Val Ala Tyr Leu Arg Ala Leu Ser
        675                 680                 685
Leu Glu Val Ala Glu Glu Ile Ala Arg Leu Glu Ala Glu Val Phe Arg
    690                 695                 700
Leu Ala Gly His Pro Phe Asn Leu Asn Ser Arg Asp Gln Leu Glu Arg
705                 710                 715                 720
Val Leu Phe Asp Glu Leu Gly Leu Pro Ala Ile Gly Lys Thr Glu Lys
                725                 730                 735
Thr Gly Lys Arg Ser Thr Ser Ala Ala Val Leu Glu Ala Leu Arg Glu
            740                 745                 750
Ala His Pro Ile Val Glu Lys Ile Leu Gln Tyr Arg Glu Leu Thr Lys
        755                 760                 765
Leu Lys Ser Thr Tyr Ile Asp Pro Leu Pro Asp Leu Ile His Pro Arg
    770                 775                 780
Thr Gly Arg Leu His Thr Arg Phe Asn Gln Thr Ala Thr Ala Thr Gly
785                 790                 795                 800
Arg Leu Ser Ser Ser Asp Pro Asn Leu Gln Asn Ile Pro Val Arg Thr
                805                 810                 815
Pro Leu Gly Gln Arg Ile Arg Arg Ala Phe Ile Ala Glu Gly Trp
            820                 825                 830
Leu Leu Val Ala Leu Asp Tyr Ser Gln Ile Glu Leu Arg Val Leu Ala
        835                 840                 845
His Leu Ser Gly Asp Glu Asn Leu Ile Arg Val Phe Gln Glu Gly Arg
    850                 855                 860
```

-continued

```
Asp Ile His Thr Glu Thr Ala Ser Trp Met Phe Gly Val Pro Arg Glu
865                 870                 875                 880

Ala Val Asp Pro Leu Met Arg Arg Ala Ala Lys Thr Ile Asn Phe Gly
            885                 890                 895

Val Leu Tyr Gly Met Ser Ala His Arg Leu Ser Gln Glu Leu Ala Ile
        900                 905                 910

Pro Tyr Glu Glu Ala Gln Ala Phe Ile Glu Arg Tyr Phe Gln Ser Phe
    915                 920                 925

Pro Lys Val Arg Ala Trp Ile Glu Lys Thr Leu Glu Glu Gly Arg Arg
930                 935                 940

Arg Gly Tyr Val Glu Thr Leu Phe Gly Arg Arg Arg Tyr Val Pro Asp
945                 950                 955                 960

Leu Glu Ala Arg Val Lys Ser Val Arg Glu Ala Ala Glu Arg Met Ala
            965                 970                 975

Phe Asn Met Pro Val Gln Gly Thr Ala Ala Asp Leu Met Lys Leu Ala
        980                 985                 990

Met Val Lys Leu Phe Pro Arg Leu  Glu Glu Met Gly Ala  Arg Met Leu
        995                 1000                1005

Leu Gln  Val His Asp Glu Leu  Val Leu Glu Ala Pro  Lys Glu Arg
    1010                1015                1020

Ala Glu  Ala Val Ala Arg Leu  Ala Lys Glu Val Met  Glu Gly Val
    1025                1030                1035

Tyr Pro  Leu Ala Val Pro Leu  Glu Val Glu Val Gly  Ile Gly Glu
    1040                1045                1050

Asp Trp  Leu Ser Ala Lys Glu
    1055                1060

<210> SEQ ID NO 11
<211> LENGTH: 983
<212> TYPE: PRT
<213> ORGANISM: Artificial Sequence
<220> FEATURE:
<223> OTHER INFORMATION: Description of Artificial Sequence: Pwo/Taq
      Chimeric polymerase

<400> SEQUENCE: 11

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160
```

```
Ser Tyr Ala Asp Glu Asn Glu Ala Lys Val Ile Thr Trp Lys Asn Ile
            165                 170                 175
Asp Leu Pro Tyr Val Glu Val Ser Ser Arg Glu Met Ile Lys
        180                 185                 190
Arg Phe Leu Arg Ile Ile Arg Glu Lys Asp Pro Asp Ile Ile Val Thr
            195                 200                 205
Tyr Asn Gly Asp Ser Phe Asp Phe Pro Tyr Leu Ala Lys Arg Ala Glu
        210                 215                 220
Lys Leu Gly Ile Lys Leu Thr Ile Gly Arg Asp Gly Ser Glu Pro Lys
225                 230                 235                 240
Met Gln Arg Ile Gly Asp Met Thr Ala Val Glu Val Lys Gly Arg Ile
                245                 250                 255
His Phe Asp Leu Tyr His Val Ile Thr Arg Thr Ile Asn Leu Pro Thr
            260                 265                 270
Tyr Thr Leu Glu Ala Val Tyr Glu Ala Ile Phe Gly Lys Pro Lys Glu
        275                 280                 285
Lys Val Tyr Ala Asp Glu Ile Ala Lys Ala Trp Glu Ser Gly Glu Asn
290                 295                 300
Leu Glu Arg Val Ala Lys Tyr Ser Met Glu Asp Ala Lys Ala Thr Tyr
305                 310                 315                 320
Glu Leu Gly Lys Glu Phe Leu Pro Met Glu Ile Gln Leu Ser Arg Leu
                325                 330                 335
Val Gly Gln Pro Leu Trp Asp Val Ser Arg Ser Ser Thr Gly Asn Leu
            340                 345                 350
Val Glu Trp Phe Leu Leu Arg Lys Ala Tyr Glu Arg Asn Glu Val Ala
        355                 360                 365
Pro Asn Lys Pro Ser Glu Glu Tyr Gln Arg Arg Leu Arg Glu Ser
    370                 375                 380
Tyr Thr Gly Gly Phe Val Lys Glu Pro Glu Lys Gly Leu Trp Glu Asn
385                 390                 395                 400
Ile Val Tyr Leu Asp Phe Arg Ala Leu Tyr Pro Ser Ile Ile Ile Thr
                405                 410                 415
His Asn Val Ser Pro Ala Phe Leu Glu Arg Leu Glu Phe Gly Ser Leu
            420                 425                 430
Leu His Glu Phe Gly Leu Leu Glu Ser Pro Lys Ala Leu Glu Glu Ala
        435                 440                 445
Pro Trp Pro Pro Pro Glu Gly Ala Phe Val Gly Phe Val Leu Ser Arg
    450                 455                 460
Lys Glu Pro Met Trp Ala Asp Leu Leu Ala Leu Ala Ala Ala Arg Gly
465                 470                 475                 480
Gly Arg Val His Arg Ala Pro Glu Pro Tyr Lys Ala Leu Arg Asp Leu
                485                 490                 495
Lys Glu Ala Arg Gly Leu Leu Ala Lys Asp Leu Ser Val Leu Ala Leu
            500                 505                 510
Arg Glu Gly Leu Gly Leu Pro Pro Gly Asp Pro Met Leu Leu Ala
        515                 520                 525
Tyr Leu Leu Asp Pro Ser Asn Thr Thr Pro Glu Gly Val Ala Arg Arg
    530                 535                 540
Tyr Gly Gly Glu Trp Thr Glu Glu Ala Gly Glu Arg Ala Ala Leu Ser
545                 550                 555                 560
Glu Arg Leu Phe Ala Asn Leu Trp Gly Arg Leu Glu Gly Glu Glu Arg
                565                 570                 575
Leu Leu Trp Leu Tyr Arg Glu Val Glu Arg Pro Leu Ser Ala Val Leu
```

```
                        580             585             590
Ala His Met Glu Ala Thr Gly Val Arg Leu Asp Val Ala Tyr Leu Arg
                595             600             605
Ala Leu Ser Leu Glu Val Ala Glu Glu Ile Ala Arg Leu Glu Ala Glu
            610             615             620
Val Phe Arg Leu Ala Gly His Pro Phe Asn Leu Asn Ser Arg Asp Gln
625             630             635             640
Leu Glu Arg Val Leu Phe Asp Glu Leu Gly Leu Pro Ala Ile Gly Lys
                645             650             655
Thr Glu Lys Thr Gly Lys Arg Ser Thr Ser Ala Ala Val Leu Glu Ala
            660             665             670
Leu Arg Glu Ala His Pro Ile Val Glu Lys Ile Leu Gln Tyr Arg Glu
            675             680             685
Leu Thr Lys Leu Lys Ser Thr Tyr Ile Asp Pro Leu Pro Asp Leu Ile
            690             695             700
His Pro Arg Thr Gly Arg Leu His Thr Arg Phe Asn Gln Thr Ala Thr
705             710             715             720
Ala Thr Gly Arg Leu Ser Ser Ser Asp Pro Asn Leu Gln Asn Ile Pro
                725             730             735
Val Arg Thr Pro Leu Gly Gln Arg Ile Arg Arg Ala Phe Ile Ala Glu
            740             745             750
Glu Gly Trp Leu Leu Val Ala Leu Asp Tyr Ser Gln Ile Glu Leu Arg
            755             760             765
Val Leu Ala His Leu Ser Gly Asp Glu Asn Leu Ile Arg Val Phe Gln
770             775             780
Glu Gly Arg Asp Ile His Thr Glu Thr Ala Ser Trp Met Phe Gly Val
785             790             795             800
Pro Arg Glu Ala Val Asp Pro Leu Met Arg Arg Ala Ala Lys Thr Ile
                805             810             815
Asn Phe Gly Val Leu Tyr Gly Met Ser Ala His Arg Leu Ser Gln Glu
            820             825             830
Leu Ala Ile Pro Tyr Glu Glu Ala Gln Ala Phe Ile Glu Arg Tyr Phe
            835             840             845
Gln Ser Phe Pro Lys Val Arg Ala Trp Ile Glu Lys Thr Leu Glu Glu
            850             855             860
Gly Arg Arg Arg Gly Tyr Val Glu Thr Leu Phe Gly Arg Arg Arg Tyr
865             870             875             880
Val Pro Asp Leu Glu Ala Arg Val Lys Ser Val Arg Glu Ala Ala Glu
                885             890             895
Arg Met Ala Phe Asn Met Pro Val Gln Gly Thr Ala Ala Asp Leu Met
            900             905             910
Lys Leu Ala Met Val Lys Leu Phe Pro Arg Leu Glu Glu Met Gly Ala
            915             920             925
Arg Met Leu Leu Gln Val His Asp Glu Leu Val Leu Glu Ala Pro Lys
            930             935             940
Glu Arg Ala Glu Ala Val Ala Arg Leu Ala Lys Glu Val Met Glu Gly
945             950             955             960
Val Tyr Pro Leu Ala Val Pro Leu Glu Val Glu Val Gly Ile Gly Glu
                965             970             975
Asp Trp Leu Ser Ala Lys Glu
                980

<210> SEQ ID NO 12
<211> LENGTH: 958
```

```
<212> TYPE: PRT
<213> ORGANISM: Artificial Sequence
<220> FEATURE:
<223> OTHER INFORMATION: Description of Artificial Sequence: Pho/Tth
      Chimeric polymerase

<400> SEQUENCE: 12

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Arg Asp Asp Ser Ala Ile
        35                  40                  45

Asp Glu Ile Lys Lys Ile Thr Ala Gln Arg His Gly Lys Val Val Arg
    50                  55                  60

Ile Val Glu Thr Glu Lys Ile Gln Arg Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Asp Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Lys Leu Thr Phe Leu Ala Val Asp Ile Glu Thr
    130                 135                 140

Leu Tyr His Glu Gly Glu Glu Phe Gly Lys Gly Pro Val Ile Met Ile
145                 150                 155                 160

Ser Tyr Ala Asp Glu Glu Gly Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Leu Ile Arg Val Ile Lys Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Leu Leu Gly Arg Asp Asn Ser Glu Pro Lys
225                 230                 235                 240

Met Gln Lys Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Thr Gly Glu Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ala Arg Leu
                325                 330                 335

Val Gly Gln Pro Val Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Tyr Glu Arg Arg Leu Arg Glu Ser
    370                 375                 380
```

```
Tyr Glu Gly Gly Tyr Val Lys Glu Pro Glu Lys Gly Ala Phe Leu Glu
385                 390                 395                 400

Arg Leu Glu Phe Gly Ser Leu Leu His Glu Phe Gly Leu Leu Glu Ala
            405                 410                 415

Pro Ala Pro Leu Glu Glu Ala Pro Trp Pro Pro Glu Gly Ala Phe
        420                 425                 430

Val Gly Phe Val Leu Ser Arg Pro Glu Pro Met Trp Ala Glu Leu Lys
        435                 440                 445

Ala Leu Ala Ala Cys Arg Asp Gly Arg Val His Arg Ala Ala Asp Pro
    450                 455                 460

Leu Ala Gly Leu Lys Asp Leu Lys Glu Val Arg Gly Leu Leu Ala Lys
465                 470                 475                 480

Asp Leu Ala Val Leu Ala Ser Arg Glu Gly Leu Asp Leu Val Pro Gly
                485                 490                 495

Asp Asp Pro Met Leu Leu Ala Tyr Leu Leu Asp Pro Ser Asn Thr Thr
            500                 505                 510

Pro Glu Gly Val Ala Arg Arg Tyr Gly Gly Glu Trp Thr Glu Asp Ala
        515                 520                 525

Ala His Arg Ala Leu Leu Ser Glu Arg Leu His Arg Asn Leu Leu Lys
    530                 535                 540

Arg Leu Glu Gly Glu Glu Lys Leu Leu Trp Leu Tyr His Glu Val Glu
545                 550                 555                 560

Lys Pro Leu Ser Arg Val Leu Ala His Met Glu Ala Thr Gly Val Arg
                565                 570                 575

Arg Asp Val Ala Tyr Leu Gln Ala Leu Ser Leu Glu Leu Ala Glu Glu
            580                 585                 590

Ile Arg Arg Leu Glu Glu Glu Val Phe Arg Leu Ala Gly His Pro Phe
    595                 600                 605

Asn Leu Asn Ser Arg Asp Gln Leu Glu Arg Val Leu Phe Asp Glu Leu
    610                 615                 620

Arg Leu Pro Ala Leu Gly Lys Thr Gln Lys Thr Gly Lys Arg Ser Thr
625                 630                 635                 640

Ser Ala Ala Val Leu Glu Ala Leu Arg Glu Ala His Pro Ile Val Glu
                645                 650                 655

Lys Ile Leu Gln His Arg Glu Leu Thr Lys Leu Lys Asn Thr Tyr Val
            660                 665                 670

Asp Pro Leu Pro Ser Leu Val His Pro Arg Thr Gly Arg Leu His Thr
        675                 680                 685

Arg Phe Asn Gln Thr Ala Thr Ala Thr Gly Arg Leu Ser Ser Ser Asp
    690                 695                 700

Pro Asn Leu Gln Asn Ile Pro Val Arg Thr Pro Leu Gly Gln Arg Ile
705                 710                 715                 720

Arg Arg Ala Phe Val Ala Glu Ala Gly Trp Ala Leu Val Ala Leu Asp
                725                 730                 735

Tyr Ser Gln Ile Glu Leu Arg Val Leu Ala His Leu Ser Gly Asp Glu
            740                 745                 750

Asn Leu Ile Arg Val Phe Gln Glu Gly Lys Asp Ile His Thr Gln Thr
        755                 760                 765

Ala Ser Trp Met Phe Gly Val Pro Pro Glu Ala Val Asp Pro Leu Met
    770                 775                 780

Arg Arg Ala Ala Lys Thr Val Asn Phe Gly Val Leu Tyr Gly Met Ser
785                 790                 795                 800

Ala His Arg Leu Ser Gln Glu Leu Ala Ile Pro Tyr Glu Glu Ala Val
                805                 810                 815
```

Ala Phe Ile Glu Arg Tyr Phe Gln Ser Phe Pro Lys Val Arg Ala Trp
            820                 825                 830

Ile Glu Lys Thr Leu Glu Gly Arg Lys Arg Gly Tyr Val Glu Thr
        835                 840                 845

Leu Phe Gly Arg Arg Tyr Val Pro Asp Leu Asn Ala Arg Val Lys
    850                 855                 860

Ser Val Arg Glu Ala Ala Glu Arg Met Ala Phe Asn Met Pro Val Gln
865                 870                 875                 880

Gly Thr Ala Ala Asp Leu Met Lys Leu Ala Met Val Lys Leu Phe Pro
                885                 890                 895

Arg Leu Arg Glu Met Gly Ala Arg Met Leu Leu Gln Val His Asp Glu
                900                 905                 910

Leu Leu Leu Glu Ala Pro Gln Ala Arg Ala Glu Val Ala Ala Leu
            915                 920                 925

Ala Lys Glu Ala Met Glu Lys Ala Tyr Pro Leu Ala Val Pro Leu Glu
            930                 935                 940

Val Glu Val Gly Met Gly Glu Asp Trp Leu Ser Ala Lys Gly
945                 950                 955

```
<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer
      sequence

<400> SEQUENCE: 13
tttcccagtc acgacgttgt aaaacgacgg                                    30

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Primer
      sequence

<400> SEQUENCE: 14
gcaccccgct tgggcagag                                                19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer
      sequence

<400> SEQUENCE: 15
tcccgcccct cctggaagac                                               20

<210> SEQ ID NO 16
<211> LENGTH: 395
<212> TYPE: PRT
<213> ORGANISM: Thermococcus pacificus

<400> SEQUENCE: 16
```

Met Ile Leu Asp Ala Asp Tyr Ile Thr Glu Asp Gly Lys Pro Val Ile
1               5                   10                  15

Arg Ile Phe Arg Lys Glu Lys Gly Glu Phe Lys Ile Glu Tyr Asp Arg
            20                  25                  30

Asn Phe Glu Pro Tyr Phe Tyr Ala Leu Leu Lys Asp Asp Ser Ala Ile
            35                  40                  45

Glu Asp Val Lys Lys Ile Thr Ala Glu Arg His Gly Thr Thr Val Arg
 50                  55                  60

Val Val Arg Ala Glu Lys Val Lys Lys Phe Leu Gly Arg Pro Ile
 65                  70                  75                  80

Glu Val Trp Lys Leu Tyr Phe Thr His Pro Gln Asp Val Pro Ala Ile
                 85                  90                  95

Arg Asp Lys Ile Arg Glu His Pro Ala Val Val Asp Ile Tyr Glu Tyr
                100                 105                 110

Asp Ile Pro Phe Ala Lys Arg Tyr Leu Ile Asp Lys Gly Leu Ile Pro
                115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
                180                 185                 190

Arg Phe Leu Arg Val Ile Lys Glu Lys Asp Pro Asp Val Leu Ile Thr
                195                 200                 205

Tyr Asn Gly Asp Asn Phe Asp Phe Ala Tyr Leu Lys Lys Arg Ser Glu
                210                 215                 220

Lys Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Ile Phe Gly Gln Pro Lys Glu
                275                 280                 285

Lys Val Tyr Ala Glu Glu Ile Thr Gln Ala Trp Glu Thr Gly Glu Gly
                290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
                355                 360                 365

Pro Asn Lys Pro Asp Glu Lys Glu Leu Ala Arg Arg Arg Glu Ser Tyr
                370                 375                 380

Ala Gly Gly Tyr Val Lys Glu Pro Glu Lys Gly
385                 390                 395

<210> SEQ ID NO 17
<211> LENGTH: 957
<212> TYPE: PRT
<213> ORGANISM: Artificial Sequence
<220> FEATURE:
<223> OTHER INFORMATION: Description of Artificial Sequence: Tpac/Taq
      Chimeric polymerase

<400> SEQUENCE: 17

```
Met Ile Leu Asp Ala Asp Tyr Ile Thr Glu Asp Gly Lys Pro Val Ile
1               5                   10                  15

Arg Ile Phe Arg Lys Glu Lys Gly Glu Phe Lys Ile Glu Tyr Asp Arg
            20                  25                  30

Asn Phe Glu Pro Tyr Phe Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
        180                 185                 190

Arg Phe Leu Arg Val Ile Lys Glu Lys Asp Pro Asp Val Leu Ile Thr
    195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
        260                 265                 270

Tyr Thr Leu Glu Ala Val Tyr Glu Ala Ile Phe Gly Gln Pro Lys Glu
    275                 280                 285

Lys Val Tyr Ala Glu Glu Ile Thr Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
        340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Glu Ser Tyr
370                 375                 380

Ala Gly Gly Tyr Val Lys Glu Pro Glu Lys Gly Ala Phe Leu Glu Arg
385                 390                 395                 400

Leu Glu Phe Gly Ser Leu Leu His Glu Phe Gly Leu Leu Glu Ser Pro
            405                 410                 415

Lys Ala Leu Glu Glu Ala Pro Trp Pro Pro Pro Glu Gly Ala Phe Val
```

```
                    420               425               430
Gly Phe Val Leu Ser Arg Lys Glu Pro Met Trp Ala Asp Leu Leu Ala
            435               440               445
Leu Ala Ala Ala Arg Gly Gly Arg Val His Arg Ala Pro Glu Pro Tyr
        450               455               460
Lys Ala Leu Arg Asp Leu Lys Glu Ala Arg Gly Leu Leu Ala Lys Asp
465               470               475               480
Leu Ser Val Leu Ala Leu Arg Glu Gly Leu Gly Leu Pro Pro Gly Asp
                485               490               495
Asp Pro Met Leu Leu Ala Tyr Leu Leu Asp Pro Ser Asn Thr Thr Pro
            500               505               510
Glu Gly Val Ala Arg Arg Tyr Gly Gly Glu Trp Thr Glu Glu Ala Gly
            515               520               525
Glu Arg Ala Ala Leu Ser Glu Arg Leu Phe Ala Asn Leu Trp Gly Arg
            530               535               540
Leu Glu Gly Glu Glu Arg Leu Leu Trp Leu Tyr Arg Glu Val Glu Arg
545               550               555               560
Pro Leu Ser Ala Val Leu Ala His Met Glu Ala Thr Gly Val Arg Leu
                565               570               575
Asp Val Ala Tyr Leu Arg Ala Leu Ser Leu Glu Val Ala Glu Glu Ile
                580               585               590
Ala Arg Leu Glu Ala Glu Val Phe Arg Leu Ala Gly His Pro Phe Asn
            595               600               605
Leu Asn Ser Arg Asp Gln Leu Glu Arg Val Leu Phe Asp Glu Leu Gly
            610               615               620
Leu Pro Ala Ile Gly Lys Thr Glu Lys Thr Gly Lys Arg Ser Thr Ser
625               630               635               640
Ala Ala Val Leu Glu Ala Leu Arg Glu Ala His Pro Ile Val Glu Lys
                645               650               655
Ile Leu Gln Tyr Arg Glu Leu Thr Lys Leu Lys Ser Thr Tyr Ile Asp
                660               665               670
Pro Leu Pro Asp Leu Ile His Pro Arg Thr Gly Arg Leu His Thr Arg
            675               680               685
Phe Asn Gln Thr Ala Thr Ala Thr Gly Arg Leu Ser Ser Ser Asp Pro
            690               695               700
Asn Leu Gln Asn Ile Pro Val Arg Thr Pro Leu Gly Gln Arg Ile Arg
705               710               715               720
Arg Ala Phe Ile Ala Glu Glu Gly Trp Leu Leu Val Ala Leu Asp Tyr
                725               730               735
Ser Gln Ile Glu Leu Arg Val Leu Ala His Leu Ser Gly Asp Glu Asn
            740               745               750
Leu Ile Arg Val Phe Gln Glu Gly Arg Asp Ile His Thr Glu Thr Ala
            755               760               765
Ser Trp Met Phe Gly Val Pro Arg Glu Ala Val Asp Pro Leu Met Arg
            770               775               780
Arg Ala Ala Lys Thr Ile Asn Phe Gly Val Leu Tyr Gly Met Ser Ala
785               790               795               800
His Arg Leu Ser Gln Glu Leu Ala Ile Pro Tyr Glu Glu Ala Gln Ala
                805               810               815
Phe Ile Glu Arg Tyr Phe Gln Ser Phe Pro Lys Val Arg Ala Trp Ile
                820               825               830
Glu Lys Thr Leu Glu Glu Gly Arg Arg Arg Gly Tyr Val Glu Thr Leu
            835               840               845
```

```
Phe Gly Arg Arg Arg Tyr Val Pro Asp Leu Glu Ala Arg Val Lys Ser
    850             855             860

Val Arg Glu Ala Ala Glu Arg Met Ala Phe Asn Met Pro Val Gln Gly
865             870             875             880

Thr Ala Ala Asp Leu Met Lys Leu Ala Met Val Lys Leu Phe Pro Arg
            885             890             895

Leu Glu Glu Met Gly Ala Arg Met Leu Leu Gln Val His Asp Glu Leu
            900             905             910

Val Leu Glu Ala Pro Lys Glu Arg Ala Glu Ala Val Ala Arg Leu Ala
        915             920             925

Lys Glu Val Met Glu Gly Val Tyr Pro Leu Ala Val Pro Leu Glu Val
    930             935             940

Glu Val Gly Ile Gly Glu Asp Trp Leu Ser Ala Lys Glu
945             950             955
```

THERMOSTABLE CHIMERIC NUCLEIC ACID POLYMERASES AND USES THEREOF

Cross Reference to Related Application

This application is a continuation of international application No. PCT/EP01/01790, filed Feb. 16, 2001, which is a continuation-in-part of U.S. Ser. No. 09/506,153, filed Feb. 17, 2000, now abandoned.

FIELD OF THE INVENTION

The present invention is in the field of molecular biology. The present invention is directed to novel thermostable chimeric enzymes useful for the generation of nucleic acids, methods for making thermostable chimeric nucleic acid polymerases, and methods useful for polymerizing nucleic acids using a thermostable chimeric nucleic acid polymerase. Specifically, the invention is directed to chimeric thermostable DNA polymerases and their uses.

BACKGROUND OF THE INVENTION

Nucleic acid polymerases are an important class of compounds that enzymatically link (polymerize) nucleotides to form larger polynucleotide chains (e.g., DNA or RNA strands). Nucleic acid polymerases typically utilize a template polynucleotide (in either a single-strand or double-strand form) for nucleic acid synthesis, as in conventional nucleic acid replication, transcription, or reverse transcription. Other nucleic acid polymerases, e.g., terminal transferase (TdT), are capable of de novo polymerization, that is, template independent nucleic acid synthesis.

All known nucleic acid polymerases possess an enzymatic domain that catalyzes the formation of a phosphodiester bond between two nucleotides, utilizing the 5' carbon triphosphate of one nucleotide and the 3' carbon hydroxyl group of another nucleotide. Nucleic acid polymerases synthesize nascent polynucleotides by linking the 5' phosphate of one nucleotide to the 3' OH group of the growing polynucleotide strand. This process is known and commonly referred to by persons skilled in the art as 5'-3' polymerization.

In addition, nucleic acid polymerases possess a wide range of ancillary chemical properties useful for nucleic acid synthesis. These properties include, but are not limited to:

product and/or template specificity (e.g., RNA or DNA); single-strand or double-strand template specificity;

processivity—a measure of the ability of a nucleic acid polymerase to generate a nascent polynucleotide from a template polynucleotide without dissociating from the template;

extension rate—a measure of the rate at which nucleotides are added to a growing polynucleotide strand;

fidelity—a measure of the accuracy (or conversely the error rate) with which a nucleic acid polymerase synthesizes a polynucleotide complementary to a template polynucleotide;

nick translation—the ability of a nucleic acid polymerase to degrade the preceding nucleotide strand of a double strand molecule simultaneous to polymerizing a nascent strand;

proofreading—the ability of a nucleic acid polymerase to remove an incorrectly linked nucleotide from a polynucleotide before further polymerization occurs; and thermostability—the ability of a nucleic acid polymerase to retain activity after exposure to elevated temperatures.

Many of these properties are the result of one or more discrete functional domains within a polymerase holoenzyme. Three extensively studied enzymatically active domains of nucleic acid polymerase include: a 5'-3' polymerase domain, responsible for polynucleotide synthesis; a 5'-3' exonuclease domain, responsible for polynucleotide digestion of the 5' end of a polynucleotide, useful for nick translation; and a 3'-5' exonuclease domain, responsible for polynucleotide digestion of the 3' end of a polynucleotide, allowing for proofreading, and thus improving the fidelity of the polymerase. Some studies indicate that selection, incorporation, and extension of the correct nucleotide, versus an incorrect nucleotide, is a variable property of the 5'-3' polymerase domain, thus affecting polymerase fidelity in concert with proofreading activity (Mendelman et al., 1990; Petruska et al., 1988).

DNA polymerases can be categorized into six families based on amino acid homology. These families consist of; pol I, pol α,SONDZEICHEN pol β, SONDZEICHEN DNA-dependent RNA polymerase, reverse transcriptase, and RNA-dependent RNA polymerase (Joyce and Steitz, 1994). Table 1 summarizes the enzymatic features of a few representative DNA polymerases.

TABLE 1

| | DNA polymerase enzymatic activity | | | | |
|---|---|---|---|---|---|
| DNA polymerase | (N terminus 5'-3' exanuclease | 3'-5' exonuclease | C terminus) 5'-3' polymerase | Thermastability | de nova polymerase |
| E. coli pol I | (+) | (+) | (+) | (−) | (−) |
| Klenaw fragment | (−) | (+) | (+) | (−) | (−) |
| E. coli pol II | (−) | (+) | (+) | (−) | (−) |
| E. coli pol III | (+) | (+) | (+) | (−) | (−) |
| T4 pol | (−) | (+) | (+) | (−) | (−) |
| T7 pol | (−) | (+) | (+) | (−) | (−) |
| M-MuLV RT | (−) | (−) | (+) | (−) | (−) |
| TdT | (−) | (−) | (+) | (+) | (+) |
| Taq pol | (+) | (−) | (+) | (+) | (−) |
| Stoffel fragment | (−) | (−) | (+) | (+) | (−) |
| Tbr pol | (+) | (−) | (+) | (+) | (−) |
| Tli pol | (−) | (+) | (+) | (+) | (−) |
| Tma pol | (−) | (+) | (+) | (+) | (−) |
| Tth pol | (+) | (−) | (+) | (+) | (−) |

TABLE 1-continued

| | DNA polymerase enzymatic activity | | | | |
|---|---|---|---|---|---|
| DNA polymerase | (N terminus) 5'-3' exanuclease | 3'-5' exonuclease | (C terminus) 5'-3' polymerase | Thermastability | de nova polymerase |
| Pfu pol | (−) | (+) | (+) | (+) | (−) |
| Psp pol | (−) | (+) | (+) | (+) | (−) |
| Pwo pol | (−) | (+) | (+) | (+) | (−) |

Because of the diversity of properties and characteristics potentially exhibited by nucleic acid polymerases generally, practitioners in the art have sought to modify, to alter, or to recombine various features of nucleic acid polymerases in an effort to develop new and useful variants of the enzyme. Initially, polymerase truncations and deletions were developed. The Klenow fragment, for example, was the first nucleic acid polymerase variant developed. Klenow fragments exist as a large C-terminal truncation of DNA polymerase I (pol I), possessing an enzymatically active 3'-5' exonuclease and 5'-3' polymerase domains, but lacking altogether the 5'-3' exonuclease domain of native pol I (Klenow and Henningsen, 1970; Jacobson et al., 1974; and Joyce and Grindley, 1983).

Since the advent of the polymerase chain reaction (PCR) methodology (including derivative methodologies such as reverse transcription PCR, or RT-PCR), resilient nucleic acid polymerases, capable of withstanding temperature spikes as high as 95° C. without a subsequent significant loss in enzymatic activity (i.e., thermostable) have become vital tools in modern molecular biology. The use of thermostable enzymes to amplify nucleic acid sequences is described in U.S. Pat. Nos. 4,683,195 and 4,683,202. A thermostable DNA polymerase from *Thermus aquaticus* (Taq) has been cloned, expressed and purified from recombinant cells (Lawyer et al., 1989; U.S. Pat. Nos. 4,889,818 and 5,079,352. PCR is also described in many U.S. patents, including U.S. Pat. Nos. 4,965,188, 4,683,195, 4,683,202, 4,800,159, 4,965,188, 4,889,818, 5,075,216, 5,079,352, 5,104,792, 5,023,171, 5,091,310, and 5,066,584.).

As depicted in Table I, Taq DNA polymerase possesses enzymatically active 5'-3' polymerase and 5'-3' exonuclease domains, but it exhibits only background levels of 3'-5' exonuclease activity (Lawyer et al., 1989; Bernard et al., 1989; Longley et al., 1990). Crystallographic data revealed that Taq polymerase contains a 3'-5' exonuclease domain (Eom et al., 1996); comparisons of the crystal structure of the Klenow fragment from Bacillus DNA polymerase I, Taq DNA polymerase, and *E. coli* DNA polymerase I have shown, however, that critical residues required to carry out a 3'-5' exonuclease activity are missing in the 3'-5' exonuclease domain of Taq DNA polymerase (Kiefer et al., 1997). Park et al. (1997), have determined that Taq DNA polymerase possesses none of three sequence motifs (Exo I, II, and III) within the 3'-5' exonuclease domain and necessary for 3'-5' exonuclease activity. Because Taq polymerase exhibits essentially no 3'-5' exonuclease activity (i.e., proofreading capability), the error rate of Taq DNA polymerase is high compared to other DNA polymerases that possess an enzymatically active 3'-5' exonuclease domain (Flaman et al., 1994). The Taq DNA polymerase structure thus comprises a 5'-3' exonuclease domain occurring at the N-terminal region of the polypeptide (residues 1-291), followed by an enzymatically inactive 3'-5' exonuclease domain (residues 292-423), and a C-terminal 5'-3' polymerase domain (Park et al., 1997).

Since Taq DNA polymerase does not possess an enzymatically active 3'-5' exonuclease domain, providing a proofreading feature to the polymerase, the use of Taq DNA polymerase becomes less desirable for most nucleic acid amplification applications, e.g., for PCR sequencing protocols or amplification for protein expression, which require complete identity of replication products to the template nucleic acid. Depending on the phase of PCR during which an error becomes incorporated into the PCR product (e.g., in an early replication cycle), the entire population of amplified DNA could contain one or more sequence errors, giving rise to a nonfunctional and/or mutant gene product. Nucleic acid polymerases that possess an enzymatically active 3'-5' exonuclease domain (i.e., proofreading activity), therefore, are especially preferred for replication procedures requiring high fidelity.

Due to the scientific and commercial importance of PCR in modern molecular biology, the reliance of PCR protocols on nucleic acid polymerases of particular characteristics, and in view of the enzymatic deficiencies of Taq polymerase, an enormous amount of research and development has focussed on developing new and useful thermostable DNA polymerase variants and/or assemblages.

One approach has been directed to the discovery and isolation of new thermophilic nucleic acid polymerases, which may possess a unique and/or improved collection of catalytic properties. As a result, thermostable nucleic acid polymerases have been isolated from a variety of biological sources, including, but not limited to, species of the taxonomic genera, Thermus, Thermococcus, Thermotoga, Pyrococcus, and Sulfolobus. These polymerases possess a variety of chemical characteristics, as illustrated in Table 1. Some of these naturally occurring thermostable DNA polymerases possess enzymatically active 3'-5' exonuclease domains, providing a natural proofreading capability and, thus, exhibiting higher fidelity than Taq DNA polymerase. Naturally occurring proofreading thermostable polymerases include: Pfu polymerase (isolated from *Pyrococcus furiosus*), Pwo polymerase (isolated from *Pyrococcus woesei*), Tli polymerase (isolated from *Thermococcus litoralis*), and Psp polymerase (isolated from Pyrococcus sp. GB-D). All of these naturally occurring thermostable polymerases are commercially available (Tli polymerase and Psp polymerase are marketed as Vent® and Deep Vent$^{SONDZEICHEN}$® DNA polymerase, respectively, by New England Biolabs, Beverly, Mass.). These DNA polymerases show slower DNA extension rates and an overall lower processivity when compared to Taq DNA polymerase, however, thus rendering these naturally occurring thermostable DNA polymerases less desirable for PCR, despite their higher fidelity.

In an effort to compensate for the deficiencies of individual thermostable polymerases, a second approach has been to develop multiple enzyme assemblages, combining, for example, Taq polymerase and a proofreading enzyme, such as Pfu polymerase or Vent$^{SONDZEICHEN}$® polymerase. These multiple-enzyme mixtures exhibit higher PCR efficiency and reduced error rates when compared to Taq polymerase alone (Barnes, 1994). Mixtures of multiple thermostable enzymes are commercially available (e.g., the Failsafe™ PCR system from Epicentre, Madison, Wis.). PCR protocols utilizing multiple polymerase mixtures are still prone to error, however, and require the practitioner to perform preliminary experimental trials, to determine special optimized solution conditions necessary for multiple-enzyme reaction mixtures.

A third approach has been to develop new and useful variants of Taq polymerase through deletion/truncation techniques. The Stoffel fragment, for example, is a 544 amino acid C-terminal truncation of Taq DNA polymerase, possessing an enzymatically active 5'-3' polymerase domain but lacking 3'-5' exonuclease and 5'-3' exonuclease activity. Other commercially available thermostable polymerase deletions include Vent$^{SONDZEICHEN}$® (exo⁻) and Deep Vent$^{SONDZEICHEN}$® (exo⁻) (New England Biolabs, Beverly, Mass.). Deletion mutations serve only to remove functional domains of a nucleic acid polymerase, however, and do not add any novel features or enzymatic properties.

Polymerase mutagenesis is yet another approach that has been attempted to develop new and useful nucleic acid polymerase variants. Park et al. (1997) performed site-directed mutagenesis of 4 amino acids in the enzymatically inactive 3'-5' exonuclease domain of Taq polymerase in an effort to activate the proofreading ability of this domain. The resultant mutant exhibited an increase of exonuclease activity over that of naturally occurring Taq polymerase. The reported increase was a mere two-fold increase above background exonuclease activity, however; an insignificant rise in exonuclease activity that is unlikely to increase PCR fidelity.

Bedford et al. (1997) developed a recombinant mesophilic DNA pol I from *E. coli*. They succeeded to insert a thioredoxin binding domain from T7 DNA polymerase into *E. coli* pol I. The inserted 76 amino acid binding domain improved polymerase binding to a template polynucleotide, thus increasing the processivity of the recombinant *E. coli* pol I but did not improve or provide any novel enzymatic activity to the polymerase.

Recently Gelfand et al. (1999) combined fusion protein technology with mutagenesis to eliminate or substantially reduce 5'-3' exonuclease activity and 3'-5' exonuclease activity in recombinant polymerases. Once again, no improved or additional enzymatic activity was provided by the fusion polymerase.

Frey et al. (1999) attempted to engineer chimeric polymerases utilizing enzymatically active domains from Taq, Tne, and *E. coli* DNA polymerases. Although they successfully substituted the non-functional 3'-5' exonuclease domain of Taq DNA polymerase with a functional 3'-5' exonuclease domain from another DNA polymerase, their resultant chimeric polymerase lost significant, if not all, enzymatic activity after only one minute at 80° C. or 95° C. (i.e., they are not thermostable), and thus are not useful for performing PCR protocols without the successive addition of fresh polymerase for each cycle.

Despite these intense research efforts, there remains a need in the art for thermostable nucleic acid polymerases that possess improved or novel assemblages of enzymatically active domains. Despite its enzymatic deficiencies, Taq DNA polymerase remains the most widely used enzyme for processing in vitro amplification of nucleic acids. In particular, there has been long felt need for a nucleic acid polymerase possessing the 5'-3' polymerization qualities of Taq polymerase, but which also possesses 3'-5' exonuclease (proofreading) activity.

SUMMARY OF THE INVENTION

In response to the long felt need for new and useful nucleic acid polymerases, a novel approach for producing thermostable nucleic acid polymerases was invented. The present invention represents the first thermostable chimeric nucleic acid polymerase, useful for continuous PCR protocols, obtained by combining at least two enzymatically active domains from different proteins by means of recombinant DNA techniques.

The present invention is directed to novel thermostable chimeric enzymes useful for the generation of nucleic acids, methods for making thermostable chimeric nucleic acid polymerases, and methods useful for polymerizing nucleic acids using a thermostable chimeric nucleic acid polymerase. The thermostable chimeric nucleic acid polymerase of the present invention comprises at least two enzymatically active domains, which are non-naturally associated. The recombinant association of the enzymatically active domains results in a composite enzyme not found in nature. The thermostable chimeric nucleic acid polymerase of the present invention possesses new or improved catalytic properties compared to nucleic acid polymerases known in the art.

The thermostable chimeric nucleic acid polymerase of the present invention offers several advantages over previous approaches to develop novel nucleic acid polymerases. The present invention provides a single enzyme that possesses a suite of chemical properties, the combination of which may not necessarily exist in nature, but nonetheless is useful in molecular biology. The chimeric nucleic acid polymerase of the present invention eliminates the need to specifically develop multiple-enzyme reaction mixtures, which are often difficult to optimize and expensive to use, and the necessity to add successive amounts of fresh enzyme during each cycle of a PCR program. The invention thus facilitates the rapid, efficient, and accurate generation of nucleic acid molecules, particularly in regard to PCR protocols.

Definitions

As used herein, an "enzymatically active domain" refers to any polypeptide, naturally occurring or synthetically produced, capable of mediating, facilitating, or otherwise regulating a chemical reaction, without, itself, being permanently modified, altered, or destroyed. Binding sites (or domains), in which a polypeptide does not catalyze a chemical reaction, but merely forms noncovalent bonds with another molecule, are not enzymatically active domains as defined herein. In addition, catalytically active domains, in which the protein possessing the catalytic domain is modified, altered, or destroyed, are not enzymatically active domains as defined herein. Enzymatically active domains, therefore, are distinguishable from other (nonenzymatic) catalytic domains known in the art (e.g., detectable tags, signal peptides, alosteric domains, etc.).

As defined herein, a 3'-5' exonuclease domain refers to any polypeptide capable of enzymatically cleaving a nucleotide from the 3' end of a di- or polynucleotide, a 5'-3' exonuclease domain refers to any polypeptide capable of enzymatically cleaving a nucleotide from the 5' end of a di- or polynucleotide, and a 5'-3' polymerase domain refers to any polypeptide capable of enzymatically linking the 5' phosphate of one nucleotide to the 3' OH group of another nucleotide.

Polypeptide domains that are "non-naturally associated", refer to specific polypeptides that are not naturally produced within a single polypeptide; that is, the polypeptide domains are not naturally translated from a common nucleic acid transcript in a naturally occurring organism. Non-naturally associated polypeptide domains include domains isolated from functionally distinct proteins, separately produced by an organism of one or more species, or synthetically generated, as well as polypeptide domains isolated from functionally similar proteins, but naturally produced by organisms of different species, or synthetically generated. The term "non-naturally associated polypeptide domains" refers to domains that are associated or fused only through human intervention; the term expressly excludes naturally occurring enzymes or fragments thereof.

As used herein, the term "chimeric protein" encompasses all proteins that contain two or more polypeptide domains that are non-naturally associated (regardless of whether the domains are naturally produced by organisms of the same species, different species, or synthetically generated). A chimeric nucleic acid polymerase of the present invention must necessarily possess two or more non-naturally associated domains, as defined herein.

The term "thermostable" generally refers to the resilience of a substance to relatively high temperature treatment. A thermostable enzyme is an enzyme that retains its definitive enzymatic activity despite exposure to relatively high temperature. A thermostable nucleic acid polymerase, as generally understood by practitioners in the art and as defined herein, refers to a polymerase that is useful for PCR protocols; i.e., not requiring successive or supplemental addition of enzyme after each high temperature step of the PCR program cycle. The chimeric nucleic acid polymerase of the present invention is thermostable, in that it is useful for PCR protocols, because it does not require successive or supplemental addition of polymerase after each high temperature step of the PCR program cycle.

A preferred thermostable chimeric polymerase of the present invention is one that allows a thermal polymerase chain reaction to proceed with only an initial supply of polymerase at the start of the PCR program. Preferably, a thermostable chimeric nucleic acid polymerase retains some measurable enzymatic activity at its normal operating temperature (typically about 72° C.) after exposure to 95° C. for three minutes. More preferably, a thermostable chimeric nucleic acid polymerase is able to withstand one minute at 95° C. without significant loss (>5% loss) in enzymatic activity. In other words, a preferred thermostable chimeric nucleic acid polymerase retains at least about 95% of its polymerase activity at its normal operating temperature (typically about 72° C.) after one minute at 95° C. Even more preferably, a thermostable chimeric nucleic acid polymerase is able to withstand three minutes at 95° C. without significant loss in enzymatic activity. A most preferred thermostable chimeric nucleic acid polymerase is able to withstand ten minutes at 90° C. and still retain at least about 50% of its enzymatic activity at its normal operating temperature. In other words, the polymerase displays a "half life" (the length of time it takes for a substance to lose one half of its initial activity) of ten minutes at 90° C. Ideally, a thermostable chimeric nucleic acid polymerase displays a half-life comparable to the half-life measurement of naturally occurring thermostable nucleic acid polymerases. For example a most desirable thermostable chimeric nucleic acid polymerase displays a half-life at 90° C. comparable to that of Taq polymerase, approximately 90 minutes.

The present invention is directed generally to all thermostable chimeric nucleic acid polymerases comprising at least two non-naturally associated enzymatically active domains. As defined herein, a nucleic acid polymerase is any enzyme that catalyzes the formation of chemical bonds between (chemically bonds) nucleotides to form polynucleotide chains, that is, any enzyme that promotes nucleic acid polymerization. The thermostable chimeric nucleic acid polymerases of the present invention include all types of nucleic acid polymerases, without limitation to product or template specificity, molecular requirements, or chemical properties (e.g., RNA vs. DNA, single strand vs. double strand, high fidelity, etc.).

One embodiment of the present invention is directed to a thermostable chimeric DNA polymerase, preferably a chimeric DNA polymerase wherein the enzymatically active domains are isolated from naturally occurring proteins from two or more species, or any mutants, variants, or derivatives thereof.

As used herein, mutant, variant, and derivative polypeptides refer to all chemical permutations of a given polypeptide, which may exist or be produced, that still retain the characteristic molecular activity that is definitive of that polypeptide.

The thermostable chimeric nucleic acid polymerase of the present invention is unexpected in view of the fact that enzymatically active domains may be isolated from a wide variety of sources, yet still retain their enzymatic activities (e.g., polymerase, exonuclease) and chemical properties (e.g., thermostability, processivity). Enzymatically active domains isolated from organisms of different taxonomic kingdoms and from completely different families of proteins may be fused to produce an entirely novel, yet functional, nucleic acid polymerase. For example, enzymatically active domains from a eubacterium polymerase of e.g., Taq polymerase may be chimerically joined with enzymatically active domains from an archaeon polymerase (e.g., Pwo, Sso, and Pho polymerases).

Retention of thermal stability in a fusion protein engineered from different thermophilic proteins is highly unexpected. Attempts to construct chimeric polymerases have failed to produce thermostable chimeric polymerases (see Frey et al., 1999). The underlying principles of thermal stability of proteins derived from thermophilic organisms are not known. Even small changes in the amino acid sequence of thermoresistant proteins result in a significant decrease in thermal stability and an associated reduction in enzymatic activity of the protein. Maintenance of, or an increase in, thermal stability of thermostable DNA polymerase has only been accomplished by truncation of a DNA polymerase (e.g., Barnes, 1995). The present invention represents the first chimeric nucleic acid polymerase, containing enzymatically active domains from different thermostable proteins, that possess thermostable properties.

In a preferred embodiment, at least one of the enzymatically active domains of the chimeric nucleic acid polymerase is isolated from a DNA polymerase produced by a thermophilic organism, preferably an organism of a genus selected from the group of genera consisting of: Thermus, Thermococcus, Thermotoga, Pyrococcus, Pyrodictium, Bacillus, Sulfolobus, and Methanobacterium. Most preferably, at least one of the enzymatically active domains of the chimeric nucleic acid polymerase is isolated from a DNA polymerase selected from the group consisting of: *Thermoplasma acidophilum* (Tac) polymerase; *Thermus aquaticus* (Taq) polymerase; *Thermococcus barossii* (Tba) polymerase; *Thermus brockianus* (Tbr) polymerase; Tfi polymerase; *Thermus flavus* (Tfl) polymerase; *Thermococcus litoralis* (Tli) polymerase; *Thermococcus pacificus* (Tpac) polymerase; *Thermus ruber* (Tru) polymerase; *Thermus thermophilus* (Tth) polymerase; *Pyrodictium abyssi* (Pab) polymerase; *Pyrococcus furiosus* (Pfu) polymerase; *Pyrococcus hellenicus* (Phe) polymerase; *Pyrococcus horikoshii* (Pho) polymerase; *Pyrococcus kodakarensis* (Pko) polymerase; Pyrococcus sp. strain KOD1 (KOD) polymerase; Pyrococcus sp. strain ES4 (ES4) polymerase; *Pyrodictium occultum* (Poc) polymerase; Pyrococcus sp. GB-D (Psp) polymerase; *Pyrococcus woesei* (Pwo) polymerase; *Thermotoga maritima* (Tma) polymerase; *Thermotoga neapolitana* (Tne) polymerase; *Bacillus sterothermophilus* (Bst) polymerase; *Sulfolobus acidocaldarius* (Sac) polymerase; *Sulfolobus solfataricus* (Sso) polymerase; *Methanobacterium thermoautotrophicum* (Mth) polymerase; and mutants, variants, and derivatives thereof.

In another embodiment of the invention, the enzymatically active domains are selected from the group consisting of: 5'-3' exonuclease domain, 3'-5' exonuclease domain, and 5'-3' polymerase domain. Preferably the enzymatically active domains are naturally occurring domains, isolated from two or more species, most preferably the enzymatically active domains are isolated from naturally occurring thermostable proteins, mutants, variants, or derivatives thereof.

Another aspect of the present invention relates to an isolated polynucleotide encoding a thermostable chimeric nucleic acid polymerase comprising at least two non-naturally associated enzymatically active domains. Preferably the enzymatically active domains are isolated from different species.

A related aspect of the invention is directed to a method for synthesizing a recombinant nucleic acid that encodes a thermostable chimeric nucleic acid polymerase comprising at least two non-naturally associated enzymatically active domains.

A further aspect of the invention relates to a vector comprising a polynucleotide that encodes a thermostable chimeric nucleic acid polymerase having at least two non-naturally associated enzymatically active domains. Preferred vectors are expression vectors, which will be suitable for production of the encoded chimeric nucleic acid polymerase in transformed host cells.

Another aspect of the invention includes a recombinant host cell transformed with a vector comprising a polynucleotide that encodes a thermostable chimeric nucleic acid polymerase possessing at least two non-naturally associated enzymatically active domains.

A related aspect of the invention is directed to a method for producing a thermostable chimeric nucleic acid polymerase comprising at least two non-naturally associated enzymatically active domains.

Another aspect of the invention is directed to a process of nucleic acid polymerization, which necessarily utilizes a thermostable chimeric nucleic acid polymerase having at least two non-naturally associated enzymatically active domains.

A related aspect of the invention is directed to a kit useful for polymerization of nucleic acid, comprising a thermostable chimeric nucleic acid polymerase having at least two non-naturally associated enzymatically active domains. Preferably, the kit further comprises at least one reagent suitable for nucleic acid polymerization. Most preferably, the kit further comprises at least one reagent selected from the group consisting of one or more additional enzymes, one or more oligonucleotide primers, a nucleic acid template, any one or more nucleotide bases, an appropriate buffering agent, a salt, or other additives useful in nucleic acid polymerization.

DETAILED DESCRIPTION OF THE INVENTION

Figure 1:
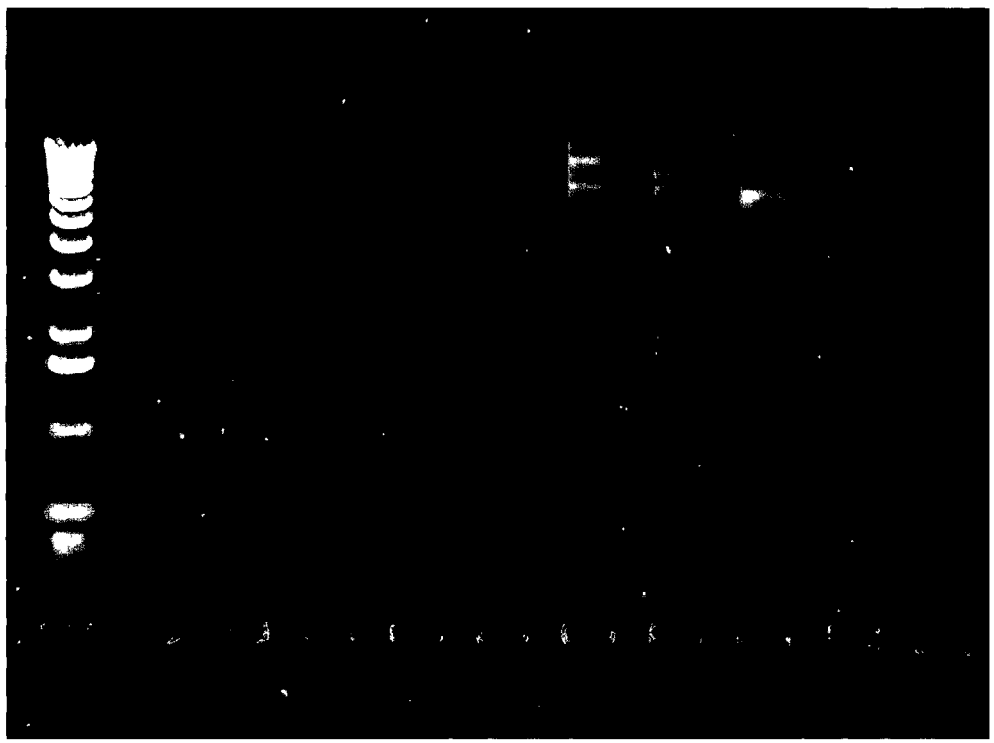
FIG. 1 is a photograph of an ethidium bromide (EtdBr)-stained agarose gel, which depicts the polymerase activity of thermostable chimeric DNA polymerases using a primer extension reaction. Lane 1 shows a nucleic acid ladder, used as a gel reference marker. Lanes 2, 6 and 10 show negative controls (without addition of polymerase). Lane 3, 4, 5 show the activity of 0.05, 0.03 and 0.01 units Taq DNA polymerase, respectively. Lanes 7-9 illustrate polymerase activity of undiluted cleared lysate, a 1:1, and 1:5 diluted cleared lysate, of a Pho/Taq chimeric polymerase, respectively.

Genetic engineering techniques were successfully employed to generate the first thermostable chimeric nucleic acid polymerase, containing enzymatically active domains, not naturally found within a single protein. The chimeric nucleic acid polymerase and methods described herein encompass all thermostable nucleic acid polymerases, without limitation to product or template specificity, molecular requirements, or chemical properties. For example, chimeric nucleic acid polymerases of the present invention include single or double strand DNA polymerases, RNA polymerases, and reverse transcriptases. Thermostable chimeric nucleic acid polymerases of the present invention may possess any number and/or combination of properties and features including, but not limited to, template depencence or independence, high processivity, high fidelity, proofreading, nick translation, and high extension rates. Persons skilled in the art will understand and appreciate that these features are due, in large part, to the presence and characteristics of discrete polypeptide domains within the holoenzyme. Essential to the chimeric nucleic acid polymerase of the present invention is that it possess at least two enzymatically active domains that are not naturally associated, and the chimeric nucleic acid is thermostable.

Enzymatically active domains may be isolated from any natural polypeptide, or may be synthetically produced. Natural polypeptides include any polypeptide found in nature, and from any organism of any taxonomic group. Enzymatically active domains useful in the present invention also include variant, mutant, or derivative forms of domains found in nature. Enzymatically active domains further include domains that may not be found in nature, e.g., polypeptides randomly generated or engineered in the laboratory or selected from a non-naturally generated library of polypeptides. For the purposes of this invention, enzymatically active domains need only necessarily possess an enzymatic activity that is functional within the chimeric nucleic acid polymerase of the invention. The thermostable chimeric nucleic acid polymerases of the present invention specifically contemplates incorporation into a nucleic acid polymerase, enzymatically active domains that are absent, inactive, or weakly active in the naturally occurring protein.

Persons skilled in the art will know and appreciate that a wide variety of enzymatic domains exist that perform the same or similar enzymatic functions. For example, DNA polymerases possess 3'-5' exonuclease domains of a wide range of enzymatic functionality; from little or no 3'-5' exonuclease activity (as seen in Taq polymerase), to fully functional 3'-5' exonuclease activity (as seen in E. coli pol I), to thermostable 3'-5' exonuclease activity (as seen in Pwo polymerase). It is understood by practitioners in the art that enzymatically active domains of individual polymerases are considered separate and distinct enzymatically active domains, as defined herein. Thus, the incorporation of an enzymatically active domain from one polymerase into a second polymerase produces, by definition, a chimeric polymerase, regardless of whether the second polymerase naturally possesses its own enzymatically active domain of similar functionality.

Preferably, genetic engineering techniques may be used to generate novel thermostable DNA polymerases possessing either 5'-3' polymerase activity and 3'-5' exonuclease activity; or 5'-3' polymerase activity, 3'-5' exonuclease activity and 5'-3' exonuclease activity derived from different thermostable DNA polymerases, e.g. Taq polymerase, Pho polymerase, Pwo polymerase, Sso polymerase, and Tpac polymerase.

Preferred thermostable chimeric nucleic acid polymerases of the present invention include a 5'-3' polymerase domain of Taq polymerase. For example, the Stoffel fragment is a 544 residue N-terminal deletion of Taq polymerase possessing an enzymatically active 5'-3' polymerase domain and an enzymatically inactive 3'-5 exonuclease domain. Generally, a Taq 5'-3' polymerase domain is at least about 544 residues in length, and includes any mutant, variant, or derivative of the Stoffel fragment of Taq polymerase, as defined herein. A 552 amino acid polypeptide, residue numbers 281-832 of Taq polymerase (SEQ ID NO:1), is an especially preferred enzymatically active Taq 5'-3' polymerase domain useful in the present invention.

Alternatively, the thermostable chimeric nucleic acid polymerases of the present invention may include a 5'-3' polymerase domain of Tth polymerase. Tth polymerase is capable of reverse transcription. Thermostable chimeric nucleic acid polymerases, which include the Tth 5'-3' polymerase domain, therefore, may be used for reverse transcription reactions (e.g., RT-PCR). Preferably, the 5'-3' polymerase domain of Tth polymerase is about 562 residues in length, including residue numbers 273-834 of Tth polymerase (SEQ ID NO:2), and includes any mutant, variant, or derivative thereof.

Preferred thermostable chimeric nucleic acid polymerases of the present invention also include an enzymatically active 3'-5' exonuclease domain of a thermostable polymerase. Preferred 3'-5' exonuclease domains include the enzymatically active 3'-5' exonuclease domains of Pho polym erase, Pwo polym erase, Sso polymerase, and Tpac polymerase. Most preferred are residues 1-396 of Pho polymerase (SEQ ID NO:3), residues 1-396 of Pwo polymerase (SEQ ID NO:4), residues 1-421 of Pwo polymerase (SEQ ID NO:5), residues 1-508 of Sso polymerase (SEQ ID NO:6), residues 1-395 of Tpac polymerase (SEQ ID NO:16), and any mutants, variants, or derivatives of any one of these 3'-5' exonuclease domains, as defined herein.

A process for synthesizing a recombinant nucleic acid encoding a thermostable chimeric nucleic acid polymerase of the invention necessarily comprises isolating at least two nucleic acid fragments each encoding at least one enzymatically active domain, which is not naturally associated with the other enzymatically active domain (i.e., derived from separate polypeptides), and genetically combining the nucleic acids of the enzymatically active domains to form a chimeric nucleic acid.

For production of thermostable chimeric nucleic acid polymerases according to the invention, the nucleic acid encoding a chimeric nucleic acid polymerase may be stably inserted into a genetic vector, preferably the nucleic acid is operably inserted into an expression vector, and most preferably the vector construct is capable of replication within a host organism, such that the nucleic acid encoding a thermostable chimeric nucleic acid polymerase is capable of being transcribed and translated into a polypeptide. A preferred mode of making the chimeric nucleic acid polymerase of the present invention includes culturing a host cell containing a nucleic acid encoding a thermostable chimeric nucleic acid polymerase under conditions suitable for expression of the chimeric nucleic acid polymerase by the host cell, and isolating the chimeric nucleic acid polymerase expressed from said cell culture.

Methods for generating recombinant nucleic acids, vector construction, host cell transformation, and polypeptide expression systems useful in the practice of this invention can involve a wide variety of modern genetic engineering techniques, tools, and biological sources that are well known in the art and routinely practiced by those skilled in the art. Exemplary techniques and methods are described in detail herein by way of preferred example, but are not limiting to the practice of the invention. The present invention incorporates by reference in their entirety techniques and supplies well known in the field of molecular biology, including, but not limited to, techniques and supplies described in the following publications:

Ausubel, F. M. et al. eds., *Short Protocols In Molecular Biology* (4th Ed. 1999) John Wiley & Sons, NY. (ISBN 0-471-32938-X).

Freshney, R. I. *Culture of Animal Cells* (1987) Alan R. Liss, Inc.

Old, R. W. & S. B. Primrose, *Principles of Gene Manipulation: An Introduction To Genetic Engineering* (3d Ed. 1985) Blackwell Scientific Publications, Boston. Studies in Microbiology; V.2:409 pp. (ISBN 0-632-01318-4).

Sambrook, J. et al. eds., *Molecular Cloning: A Laboratory Manual* (2d Ed. 1989) Cold Spring Harbor Laboratory Press, NY. Vols. 1-3. (ISBN 0-87969-309-6).

Winnacker, E. L. *From Genes To Clones: Introduction To Gene Technology* (1987) VCH Publishers, NY (translated by Horst Ibelgaufts). 634 pp. (ISBN 0-89573-614-4).

The thermostable chimeric nucleic acid polymerases described herein are especially useful for generating a desired target nucleic acid. Thermostable chimeric nucleic acid polymerases of the invention, having at least two enzymatically active domains that are not naturally associated may be utilized under conditions sufficient to allow polymerization of a nascent nucleic acid. Generally, this method includes any method of nucleic acid generation, replication, amplification, transcription, or reverse transcription known in the art that utilizes a conventional nucleic acid polymerase, wherein the nucleic acid polymerase is substituted or combined with a chimeric nucleic acid polymerase of the present invention. Preferably the method of amplification is polymerase chain reaction, utilizing a thermostable chimeric nucleic acid polymerase. PCR is described herein as an exemplary protocol capable of utilizing the compositions and methods of the present invention without limitation. Persons skilled in the art will understand that the present invention has utility in other processes requiring the polymerization of nucleic acid (e.g., RT-PCR).

PCR is a technique well known in the art. PCR is used to amplify nucleic acids by subjecting a reaction mixture to cycles of: (i) nucleic acid denaturation, (ii) oligonucleotide primer annealization, and (iii) nucleic acid polymerization. Preferred reaction conditions for amplification comprise thermocycling, i.e., alternating the temperature of the reaction mixture to facilitate each of the steps of the PCR cycle. PCR is typically extended through multiple cycles of denaturation, annealization and replication, augmented (optionally and preferably) with an initial prolonged denaturation step and a final prolonged extension (polymerization) step. To perform the repetitive steps of thermocycling, it is preferable to employ an enzyme that is capable of tolerating exposure to relatively high temperature without a subsequent significant loss in enzyme activity; i.e., a thermostable enzyme. The use of a thermostable enzyme for PCR protocols permits the repetitive steps of increasing and decreasing reaction temperatures without the need to supplement, or otherwise add, enzyme after each successive high temperature step of the PCR program cycle.

Also included in the invention is a kit that includes a thermostable chimeric nucleic acid polymerase and one or more additional reagents suitable for nucleic acid polymerization reactions. Such components may include, but are not limited to: one or more additional enzymes, one or more oligonucleotide primers, a nucleic acid template, any one or more nucleotide bases, an appropriate buffering agent, a salt, or other additives useful in nucleic acid polymerization.

Additional enzymes of the kit include any enzyme that may be used in combination with the thermostable chimeric nucleic acid polymerase of the invention. For example, multiple-polymerase kits are known in the art. Numerous polymerases are known and commercially available to persons skilled in the art, and include DNA polymerases, RNA polymerases, and reverse transcriptases (commercial suppliers include: Roche Diagnostics., Indianapolis, Ind.; Life Technologies, Inc., Rockville, Md.; New England Biolabs, Inc., Beverly, Mass.; Perkin Elmer Corp., Norwalk, Conn.; Pharmacia LKB Biotechnology, Inc., Piscataway, N.J.; Qiagen, Inc., Valencia, Calif.; Stratagene, La Jolla, Calif.).

Oligonucleotide primers useful in the present invention may be any oligonucleotide of two or more nucleotides in length. Preferably, PCR primers are about 15 to about 30 bases in length and are not palindromic (self-complementary) or complementary to other primers that may be used in the reaction mixture. Primers may be, but are not limited to, random primers, homopolymers, or primers specific to a target oligonucleotide template (e.g., a sequence specific primer). Oligonucleotide primers are oligonucleotides used to hybridize to a region of a target nucleic acid to facilitate the polymerization of a complementary nucleic acid. In PCR protocols, primers serve to facilitate polymerization of a first nucleic acid molecule complementary to a portion of an oligonucleotide template, and also to facilitate replication of the oligonucleotide. Any primer may be synthesized by a practitioner of ordinary skill in the art or may be ordered and purchased from any of a number of commercial venders (e.g., from Roche Diagnostics, Indianapolis, Ind.; Life Technologies, Inc., Rockville, Md.; New England Biolabs, Inc., Beverly, Mass.; Pharmacia LKB Biotechnology, Inc., Piscataway, N.J.). It will be understood that a vast array of primers may be useful in the present invention, including those not specifically disclosed herein, without departing from the scope or preferred embodiments thereof.

A nucleic acid template is defined as any polynucleotide molecule used to provide a nucleic acid sequence from which a polynucleotide complementary to the template may be generated. The synthesis of DNA from a DNA template may be accomplished according to the invention by utilizing a thermostable chimeric DNA polymerase. The synthesis of RNA from a DNA template may be accomplished according to the invention by utilizing a thermostable chimeric RNA polymerase. The synthesis of DNA from an RNA template may be accomplished according to the invention by utilizing a thermostable chimeric nucleic acid polymerase that exhibits reverse transcriptase activity.

Nucleotide bases useful in the present invention may be any nucleotide useful in the polymerization of a nucleic acid. Nucleotides may be naturally occurring, unusual, modified, derivative, or artificial. Nucleotides may be unlabeled, or detectably labeled by methods known in the art (e.g., using radioisotopes, vitamins, fluorescent or chemiluminescent moieties, digoxigenin). Preferably the nucleotides are deoxynucleoside triphosphates, dNTPs (e.g., dATP, dCTP, dGTP, dTTP, dITP, dUTP, α-thioSONDZEICHEN-dNTPs, biotin-dUTP, fluorescein-dUTP, digoxigenin-dUTP, 7-deaza-dGTP). dNTPs are also well known in the art and are commercially available (e.g., from Roche Diagnostics, Indianapolis, Ind.; New England Biolabs, Inc., Beverly, Mass.; Pharmacia LKB Biotechnology, Inc., Piscataway, N.J.).

Buffering agents and salts useful in the present invention provide appropriate stable pH and ionic conditions for nucleic acid synthesis. A wide variety of buffers and salt solutions and modified buffers are known in the art that may be useful in the present invention, including agents not specifically disclosed herein. Preferred buffering agents include, but are not limited to, TRIS, TRICINE, BIS-TRICINE, HEPES, MOPS, TES, TAPS, PIPES, CAPS. Preferred salt solutions include, but are not limited to solutions of; potassium chloride, potassium acetate, potassium sulfate, ammonium sulfate, ammonium chloride, ammonium acetate, magnesium chloride, magnesium acetate, magnesium sulfate, manganese acetate, sodium chloride, sodium acetate, lithium chloride, and lithium acetate.

Other additives capable of facilitating nucleic acid generation and amplification, other than those disclosed for the first time by this invention, are known in the art. In accordance with the compositions and methods of this invention, one or more of these additives may be incorporated in a DNA/RNA polymerization kit according to the present invention to optimize the generation and replication of polynucleotides. Additives may be organic or inorganic compounds. Agents useful in the present invention include, but are not limited to, polypeptides such as phosphatase, human serum albumin, bovine serum albumin (BSA), ovalbumin, albumax, casein, gelatin, collagen, globulin, lysozyme, transferrin, α-lactalbumin, β-lactoglobulin, phosphorylase b, myosin, actin, β-galactosidase, lectins, *E. coli* single-stranded binding (SSB) protein, phage T4 gene 32 protein, and the like, or fragments or derivatives thereof. Examples of nonpolypeptide additives include, but are not limited to; homopolymeric nucleic acid, heteropolymeric nucleic acid, tRNA, rRNA, sulfur-containing compounds, acetate-containing compounds, dimethylsulfoxide (DMSO), glycerol, formamide, betain, tetramethylammonium chloride (TMAC), polyethylene glycol (PEG), Tween 20, NP 40, ectoine, and polyoles.

It will be readily apparent to those skilled in the art that other suitable modifications and adaptations of the compositions and methods of the invention described herein are obvious and may be made without departing from the scope of the invention or the embodiments disclosed herein. Having now described the present invention in detail, the same will be more clearly understood by reference to the following examples, which are included for purposes of illustration only and are not intended to be limiting of the invention.

EXAMPLE 1

Construction of a Thermostable Chimeric DNA Polymerase Gene

Chimeric thermostable DNA polymerase constructs containing enzymatically active domains from different (source) thermostable DNA polymerases were generated using recombinant DNA techniques. The 3'-5' exonuclease domain of various thermostable polymerases were recombinantly linked to the 5'-3' polymerase domain of Taq polymerase or Tth polymerase. The particularly preferred enzymatic domains and domain borders, described herein in detail, were selected and tested as preferred embodiments, and are not to be considered limiting in scope of the thermostable chimeric nucleic acid polymerase of the invention, or the enzymatically active domains useful therein.

Appropriate microbial strains or genomic DNA preparations, from which the enzymatically active domains used in the construction of chimeric nucleic acid polymerase were isolated, were purchased from commercial suppliers, e.g., from DSMZ GmbH (Deutsche Sammlung von Mikroorganismen und Zellkulturen GmbH), Braunschweig, Germany. Specifically chosen strains included *Thermus aquaticus* (order # DSM 625), *Thermus thermophilus* (order # DSM 579), *Pyrococcus furiosus* (order # DSM 3638), *Pyrococcus woesei* (order # DSM 3773), *Pyrococcus horikoshii* (order # DSM 3638), *Sulfolobus solfataricus* (order # DSM 5833), and *Thermococcus pacificus* (order # DSM 10394). A multiplicity of genomic DNA extraction, purification, and isolation techniques useful to obtain the desired enzymatically active domains are well known in the art.

Modified PCR amplification techniques and/or cloning procedures such as restriction digestion and ligation using appropriate enzymes were used to obtain the chimeric DNA polymerase constructs. Primers appropriate to amplify polynucleotides encoding particular enzymatic domains from the source thermostable DNA polymerases were synthesized according to the nucleotide sequences of the source thermostable DNA polymerase. DNA sequences of the source thermostable DNA polymerases are published in GenBank. The synthesis of oligonucleotide primers is well known to practitioners in the art, and may also be ordered from commercial oligonucleotide suppliers (e.g., Life Technologies, Gaithersburg, Md.).

PCR primers were of special design. The primers contained a nucleotide sequence complementary to the terminal region of a particular enzymatic domain of interest within a source DNA polymerase. The primers also contained a non-complementary nucleotide sequence region as well to provide; i) an appropriate restriction enzyme site, to facilitate genetic manipulation (e.g., vector insertion), or ii) sequence information (e.g., complementarity), to facilitate fusion to a second, non-naturally associated enzymatic domain. For example, primers designed to facilitate fusion of a 3'-5' exonuclease domain to a 5'-3' polymerase domain contained a sequence, one half of which was complementary to a terminal region of the 3'-5' exonuclease domain of interest (e.g., residues 388-396 of Pho polymerase) and one half of which was complementary to a terminal region of the 5'-3' polymerase domain (e.g., residues 281-288 of Taq polymerase).

As an initial step, various enzymatic domains were amplified by PCR. The PCR reaction mixture contained: 2.5 units of Taq polymerase (Qiagen, Valencia, Calif.) and 0.1 to 0.2 units of Pfu polymerase (Stratagene, La Jolla, Calif.); an appropriate amount of the specially designed primers, as described above (0.2 to 1.0 μM); genomic DNA isolated from the appropriate microorganism containing the source thermostable polymerase; and 200 μM of each dNTP in a 1×PCR buffer (Qiagen, Valencia, Calif.). A 3-step PCR cycling program was run, consisting of an initial denaturation step at 94° C., an annealing step and an extension step. The PCR ran for 25-35 cycles, depending upon the desired amount of product. The size of the PCR product was checked by agarose gel electrophoresis against an appropriate DNA size marker. The correctly sized PCR product was gel-purified using the QIAquick™ Gel Extraction Kit (Qiagen, Valencia, Calif.).

Once isolation and amplification of the polynucleotides encoding the enzymatic domains chosen for chimeric polymerase construction were obtained, the component enzymatic domains were combined, in equivalent concentrations, in a composite PCR reaction, together with 2-5 units of Pfu polymerase (Stratagene, La Jolla, Calif.), and 200 μM of each dNTP in 1×PCR buffer (Qiagen, Valencia, Calif.). This PCR mixture did not contain any primer oligonucleotides. This reaction mixture was subjected to 10 to 15 PCR cycles.

During the composite PCR, the single strand polynucleotides encoding each of the enzymatically active domains hybridize at their respective terminal regions of complementarity (due to the specially designed primers as described above). The hybridized single strand polynucleotides encoding each of the enzymatically active domains form a single composite polynucleotide template, thus serving as primers for each other. Pfu polymerase extends the 3' terminal end of each of the enzymatically active domains, creating a single polynucleotide containing the chimeric DNA polymerase gene construct.

After the initial 10 to 15 cycles of chimeric DNA polymerase gene construction, oligonucleotide primers, appropriate to amplify the full-length chimeric DNA polymerase gene, were added to the PCR mixture. The PCR ran for 20-30 additional cycles, depending upon the desired amount of chimeric DNA polymerase PCR product. The size of the PCR product was checked by agarose gel electrophoresis and the correctly sized PCR product was gel-purified as described above.

The purified chimeric DNA polymerase gene was then subjected to restriction digestion with the appropriate restriction enzyme to cut the polynucleotide at restriction sites located at the terminal ends of the chimeric DNA polymerase gene. These sites were originally generated by the specially designed primers described above.

EXAMPLE 1.1

Construction of a Pho/Taq Thermostable Chimeric DNA Polymerase Gene

A polynucleotide encoding the enzymatically active 3'-5' exonuclease domain of Pho DNA polymerase was linked to a polynucleotide encoding the enzymatically active 5'-3' polymerase domain and the nonfunctional 3'-5' exonuclease domain of Taq DNA polymerase. A polynucleotide encoding amino acids 271-832 (SEQ ID NO:7) of Taq DNA polymerase was recombinantly linked to the 3' end of a polynucleotide encoding amino acids 1-396 (SEQ ID NO:3) of Pho DNA polymerase following the procedures detailed in Example 1 above, producing a polynucleotide that encodes a novel Pho/Taq thermostable chimeric DNA polymerase (SEQ ID NO:8).

EXAMPLE 1.2

Construction of a Pwo/Taq Thermostable Chimeric DNA Polymerase Gene

A polynucleotide encoding the enzymatically active 3'-5' exonuclease domain of Pwo DNA polymerase was linked to a polynucleotide encoding the enzymatically active 5'-3' polymerase domain of Taq DNA polymerase. A polynucleotide encoding amino acids 271-832 (SEQ ID NO:7) of Taq DNA polymerase was recombinantly linked to the 3' end of a polynucleotide encoding amino acids 1-396 (SEQ ID NO:4) of Pwo DNA polymerase following the procedures detailed in Example 1 above, producing a polynucleotide that encodes a novel Pwo/Taq thermostable chimeric DNA polymerase (SEQ ID NO:9).

EXAMPLE 1.3

Construction of a Sso/Taq Thermostable Chimeric DNA Polymerase Gene

A polynucleotide encoding the enzymatically active 3'-5' exonuclease domain of Sso DNA polymerase was linked to a polynucleotide encoding the enzymatically active 5'-3' polymerase domain of Taq DNA polymerase. A polynucleotide encoding amino acids 281-832 (SEQ ID NO:1) of Taq DNA polymerase was recombinantly linked to the 3' end of a polynucleotide encoding amino acids 1-508 (SEQ ID NO:6) of Sso DNA polymerase following the procedures detailed in Example 1 above, producing a polynucleotide that encodes a novel Sso/Taq thermostable chimeric DNA polymerase (SEQ ID NO:10).

This chimeric construct, possessing a smaller Taq 5'-3' polymerase domain than that used in Examples 1.1 and 1.2, also demonstrates that specifically determined domain borders of an enzymatic domain are not essential to the invention. What is essential for the domain is that it retain its definitive enzymatic activity.

EXAMPLE 1.4

Construction of a Tpac/Taq Chimeric DNA Polymerase Gene

A polynucleotide encoding the enzymatically active 3'-5' exonuclease domain of Tpac DNA polymerase was linked to a polynucleotide encoding the enzymatically active 5'-3' polymerase domain of Taq DNA polymerase. A polynucleotide encoding amino acids 271-832 (SEQ ID NO:7) of Taq DNA polymerase was recombinantly linked to the 3' end of a polynucleotide encoding amino acids 1-395 (SEQ ID NO:16) of Tpac DNA polymerase following the procedures detailed in Example 1 above, producing a polynucleotide that encodes a novel Tpac/Taq chimeric DNA polymerase (SEQ ID NO:17).

EXAMPLE 1.5

Construction of Variant Thermostable Chimeric DNA Polymerase Genes

To further demonstrate that a thermostable chimeric nucleic acid polymerase may be generated using an enzymatically active domain of varying domain borders (provided the enzymatic activity of the domain is retained), a Pwo/Taq chimeric DNA polymerase variant of the thermostable chimeric polymerase generated in Example 1.2 was constructed. This variant construct comprised a polynucleotide encoding amino acids 271-832 (SEQ ID NO:7) of Taq DNA polymerase recombinantly linked to the 3' end of a polynucleotide encoding amino acids 1-421 (SEQ ID NO:5) of Pwo DNA polymerase following the procedures detailed in Example 1 above, producing a polynucleotide that encodes a second novel Pwo/Taq thermostable chimeric DNA polymerase (SEQ ID NO:11).

EXAMPLE 1.6

Construction of a Pho/Tth Thermostable Chimeric DNA Polymerase Gene

To demonstrate that a thermostable chimeric nucleic acid polymerase may be generated using an enzymatically active polymerase domain other than that of Taq polymerase, a polynucleotide encoding the enzymatically active 3'-5' exonuclease domain of Pho DNA polymerase was linked to a polynucleotide encoding the enzymatically active 5'-3' polymerase domain of Tth DNA polymerase. A polynucleotide encoding amino acids 273-834 (SEQ ID NO:2) of Tth DNA polymerase was recombinantly linked to the 3' end of a polynucleotide encoding amino acids 1-396 (SEQ ID NO:3) of Pho DNA polymerase following the procedures detailed in Example 1 above, producing a polynucleotide that encodes a novel Pho/Tth thermostable chimeric DNA polymerase (SEQ ID NO:12).

This chimeric construct, possessing a Tth 5'-3' polymerase domain that is also capable of reverse transcription activity, also demonstrates a thermostable chimeric nucleic acid polymerase of the present invention useful for RT-PCR protocols.

EXAMPLE 1.7

Construction of a Thermostable Chimeric DNA Polymerase Gene Encoding More Than Two Enzymatically Active Domains The chimeric nucleic acid polymerase gene of the invention may encode two or more enzymatically active domains, of which two more domains are non-naturally occurring. In addition the enzymatically active domains may be derived from any polypeptide source naturally occurring or synthetically produced.

For example, the practitioner may wish to construct a thermostable chimeric nucleic acid polymerase possessing both the 5'-3' polymerase domain and the 5'-3' exonuclease domain of Taq polymerase, as well as the 3'-5' exonuclease domain of another polymerase (e.g., Pho polymerase). In this instance, a polynucleotide encoding the 5'-3' exonuclease domain of Taq polymerase (known to be contained within amino acids 1-291 of Taq polymerase) would be recombinantly linked to 5' end of a polynucleotide encoding the 3'-5' exonuclease domain of Pho polymerase (e.g., SEQ ID NO: 3) and the 5'-3' polymerase domain of Taq DNA polymerase (e.g., SEQ ID NOs: 1 or 7), which was earlier demonstrated in Examples 1.1 and 1.5.

EXAMPLE 2

Construction of a Thermostable Chimeric DNA Polymerase Vector

The isolated chimeric DNA polymerase genes of Examples 1.1 through 1.6 were each ligated into a vector, linearized using the appropriate restriction enzyme. Ligation was performed overnight at 16° C. using T4 DNA ligase and an appropriate buffer (Life Technologies, Gaithersburg, Md.) in a final volume of 20 µl.

EXAMPLE 3

Construction of a Thermostable Chimeric DNA Polymerase Host Cell

The ligated recombinant vectors of Example 2 were used to transform calcium-competent M15[pRep4] cells (Qiagen, Valencia, Calif.) or DH5SONDZEICHENα competent cells. Aliquots of the transformation mixture were spread onto agar plates containing ampicillin and kanamycin (for M15 [pRep4] cells), or ampicillin only (for DH5α competent cells), and incubated overnight at 37° C.

Colonies of successfully transformed cells were transferred to LB media containing the appropriate antibiotic selection, and incubated overnight. Plasmid isolation preparations were performed using QIAprep™ Spin Kit or Plasmid Midi Kit (both from Qiagen, Valencia, Calif.). Presence of the chimeric DNA polymerase gene was verified by restriction digest analysis and the chimeric DNA polymerase gene sequenced by techniques well known in the art.

The chimeric DNA polymerase genes were cloned into either pQE-30 or pQE-31 expression vectors (Qiagen, Valencia, Calif.) containing a six-histidine tag sequence preceding the respective DNA polymerase sequence.

EXAMPLE 4

Expression and Purification of a Thermostable Chimeric DNA Polymerase

Thermostable chimeric DNA polymerase gene expression of the successfully transformed host cells from Example 3, was induced by IPTG. Harvested cells were lysed by sonification and lysozyme treatment or a simple heat treatment. Chimeric His-tagged protein was purified in batch format using Ni-NTA agarose (Qiagen, Valencia, Calif.) following standard protocol procedures.

Eluates were ultrafiltrated using Nanosep$^{SONDZEICHEN}$® ultrafiltration units (Pall Deutschland GmbH Holding, Dreieich, Germany). Alternatively, heat treated cleared lysate was centrifuged through Ultrafree filterunits 300.000 (Sigma, Deisenhofen, Germany), to remove contaminating nucleic acids, and was subsequently concentrated using Nanosep$^{SONDZEICHEN}$® or Microsep$^{SONDZEICHEN}$® ultrafiltration units (Pall Deutschland GmbH Holding, Dreieich, Germany).

Concentrated samples were mixed with a storage buffer containing 20 mM TrisHCl (pH 8.0 at 20° C.), 100 mM KCl, 1 mM EDTA, 0.5% (v/v) Nonidet P-40 substitute, 0.5% (v/v) Tween 20 and 50% (v/v) glycerol. Chimeric polymerase preparations were stored at −20° C. In some cases, the cleared lysate of the polymerase preparation was directly used for subsequent analysis; chimeric polymerase preparations were then stored at +4° C.

EXAMPLE 5

5'-3' Polymerase Activity of Thermostable Chimeric DNA Polymerases

To demonstrate the polymerase activity of thermostable chimeric DNA polymerases produced from Example 4, an assay for measuring primer extension activity was performed. This assay is based on the difference in mobility of single- versus double-strand DNA molecules on an agarose gel in the presence of a DNA intercalating dye. Annealing of a primer to a single-stranded DNA molecule creates a priming site for a DNA polymerase. The primer is then extended by the polymerase, converting the single-strand DNA into double-strand molecules. The extension rate is dependent upon the polymerase used. The final amount of DNA extension (i.e., polymerization) is dependent on the amount of polymerase provided, the extension rate of the polymerase, and the length of time the reaction is allowed to proceed.

All polymerization reaction mixtures contained 50 ng M13 mp18 DNA (20 fmol; 7250 nt), 0.1 µM 30-mer oligonucleotide primer 5'-TTTCCCAGTCACGACGTTGTAAAAC-GACGG-3' (SEQ ID NO: 13), and 50 µM of each dNTP in 10 µl of 10 mM Tris HCl.

Polymerization reactions containing Taq DNA polymerase and a thermostable chimeric DNA polymerase were performed in 1×PCR buffer (Qiagen, Valencia, Calif.).

Taq DNA polymerase was used for external standard reactions (0.05, 0.03, 0.01 units) in order to determine polymerase activity of the thermostable chimeric DNA polymerases. DNA polymerases were diluted in the reaction buffer containing 1 µg/ml bovine serum albumin (BSA) to compensate for possible protein interactions with the surface of the polypropylene tube.

The assay was performed in a MJ Research PTC-200 Thermocycler (Biozym, Hess. Oldendorf, Germany) or a Biometra Unoll Thermocycler (Biometra, Göttingen, Germany). The thermal program consisted of a 10 sec. denaturation step 94° C.; a 30 sec. annealing step at 55° C.; and a 3 min. polymerization step at 72° C. Heating of the reaction mixture to 94° C. was done to destroy possible secondary structures of the single-stranded M13 DNA and to facilitate specific primer annealing during the lowering of reaction temperature to 55° C.

Results of primer extension reactions at 72° C. were reproducible. After completing the reaction, reaction products were mixed with 1 µl gel loading solution (50% Glycerol, 1×TAE buffer, 0.02 mg/ml Bromphenol blue) and loaded on a 1% agarose gel containing 0.5 µg/ml ethidium bromide. The gel was run at 80 mA for 15 min in 1×TAE buffer. These conditions facilitated discrimination between extended-(ds) and non-extended (ss) M13 DNA fragments. The results, as represented in FIG. 1, illustrate the polymerase activity of the thermostable chimeric polymerase is comparable to that of wild type Taq polymerase.

EXAMPLE 6

Thermostability of Chimeric DNA Polymerases

The primer extension assay described in Example 5 was also used to measure the resilience of chimeric DNA polymerases to thermal degradation (i.e., thermostability). Heat-treatment of chimeric DNA polymerases (0.2 units) consisted of incubation of the enzyme for 0, 10, 15, 30, 60, 90 and 120 min at 90° C., followed by primer extension at 72° C. Polymerase activity of heat-treated chimeric polymerase was compared to untreated chimeric DNA polymerase based on the amount of polymerized (i.e., double strand) M13 DNA. The same assay was performed, under identical reaction conditions, on identical amounts of Taq DNA polymerase, as a standard. A control consisted of a polymerase reaction mixture, without any DNA polymerase. After completing the reaction, reaction products were mixed with 1 µl gel loading solution (50% Glycerol, 1×TAE buffer, 0.02 mg/ml Bromphenol blue), and loaded on a 1% agarose gel containing 0.5 µg/ml ethidium bromide. The gel was run at 80 mA for 15 min in 1×TAE buffer. The results, presented in FIG. 2 and quantified in Table 2 below, are representative of the thermostability assay.

TABLE 2

Thermostability of chimeric polymerase compared to Taq Dolymerase

| Incubation at 90° C. (min.) | Pho/Taq Chimeric Polymerase % Activity | Taq Polymerase % Activity |
| --- | --- | --- |
| 0 | 100 | 100 |
| 10 | 84 | 99 |
| 15 | 84 | 89 |
| 30 | 82 | 74 |
| 60 | 66 | 69 |
| 90 | 53 | 31* |
| 120 | 45 | 43 |

*single non-reproducible data; value expected to be higher

Figure 2:
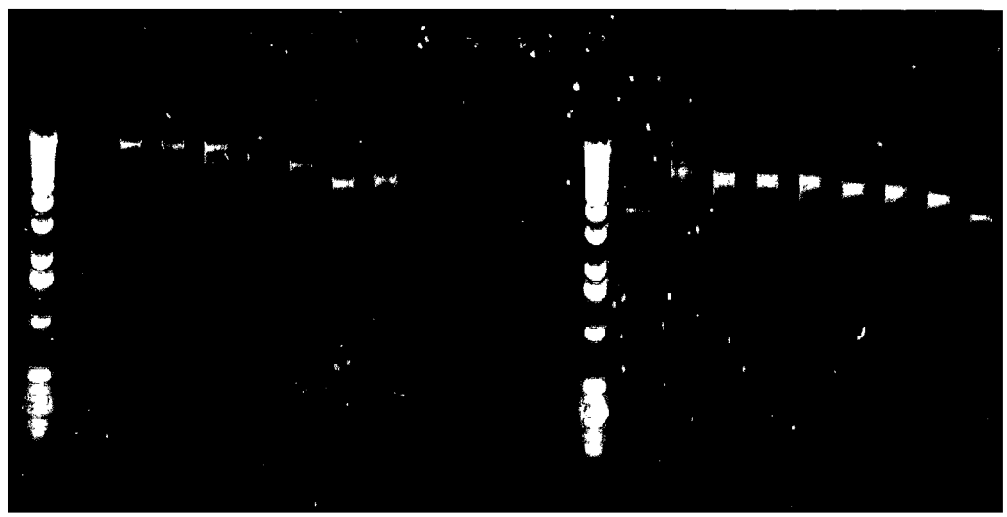
FIG. 2 is a photograph of an ethidium bromide (EtdBr)-stained agarose gel, which depicts the thermostability of a thermostable chimeric DNA polymerase compared to Taq DNA polymerase, using a primer extension reaction. DNA polymerases were incubated for various time spans at 90° C. and assayed for remaining polymerase activity. Lanes 1 and 11 show a nucleic acid ladder, used as a gel reference marker. Lanes 2, 10, 12, and 20 represent negative control reactions (without addition of polymerase). Lanes 3-9 and lanes 13-19 illustrate DNA polymerase activity after incubation of Taq DNA polymerase and a Pho/Taq chimeric DNA polymerase at 90° C. for 0, 10, 15, 30, 60, 90, and 120 min, respectively.

FIG. 2 and Table 2 confirm the thermostability of the chimeric polymerase of the present invention. Table 2 illustrates that although the activity of the chimeric DNA polymerase shows an initial drop in activity (within the first 10 min at 90° C.) greater than that of Taq DNA polymerase, the overall thermostability is comparable to Taq DNA polymerase. Chimeric DNA polymerase of the invention displays the same half life at 90° C. as Taq DNA polymerase (approximately 90 min).

The thermostability assay was also performed under extreme temperature conditions. The primer extension assay was run after heat-treatment at 95° C. for 0, 3, 5, and 10 min. The results, quantified in Table 3 below, are representative of the 95° C. thermostability assay, and further confirm that the chimeric DNA polymerase of the present invention is highly thermostable.

TABLE 3

Thermostability of chimeric polymerase

| Incubation at 95° C. (min.) | Pho/Taq Chimeric Polymerase % Activity |
| --- | --- |
| 0 | 100 |
| 3 | 100 |
| 5 | 86 |
| 10 | 86 |

These results confirm the thermostability of the chimeric DNA polymerase of the present invention, making it useful for in vitro reactions under heat denaturing conditions such as PCR, without requiring successive addition of enzyme at each cycle of the PCR program.

EXAMPLE 7

3'-5' Exonuclease Activity of Thermostable Chimeric DNA Polymerases

Fidelity of DNA replication is based on a two step process: misinsertion and misextension. In PCR, if the DNA polymerase inserts an incorrect nucleotide, and the resulting 3'-mismatched terminus of the growing DNA chain is not extended, the truncated primer extension product cannot be amplified during subsequent PCR cycles since the downstream primer binding site is missing. Additionally, mismatched termini are less efficiently extended than DNA ends harboring the complementary base. DNA polymerases possessing an enzymatically active 3'-5' exonuclease domain are capable of removing a misincorporated nucleotide, thus increasing fidelity of the PCR product and increasing primer extension efficiency.

A PCR and restriction endonuclease digestion assay, developed to assess the ability of thermostable DNA polymerases to remove mismatched primer termini by 3'-5' exonuclease activity, was performed using the protocol disclosed in U.S. Pat. No. 5,491,086 (incorporated by reference). Wild type primers, perfectly matching the BamHI restriction enzyme recognition sequence in the Taq polymerase gene, and mutant primers, possessing a 3'-mismatch (employing every possible combination) to the first nucleotide of the BamHI restriction enzyme recognition sequence, were used in side-by-side PCR trials.

Wild type primers to 5'-GCACCCCGCTTGGGCAGAG-3' (SEQ ID NO:14) and 5'-TCCCGCCCCTCCTGGAA-GAC-3' (SEQ ID NO:15) yield a 151 bp PCR product that becomes digested upon incubation with BamHI restriction enzyme, generating a 132 bp and 19 bp fragment.

Three forward primers containing a single 3'-mismatched nucleotide representing a C:A, C:T, and C:C mismatch to SEQ ID NO:14 were used as mutant primers. Any extension product from these mutant primers would corrupt the BamHI restriction site, rendering the resulting PCR products unaffected by BamHI digestion, thus leaving the 151 bp PCR product intact. The presence of an enzymatically active 3'-5' exonuclease domain, would correct the 3'-mismatched nucleotide of the mutant primer, however, thus restoring the BamHI restriction site, rendering the PCR product susceptible to BamHI digestion, thus producing the 132 bp and 19 bp digestion fragments.

Using this PCR fidelity assay, the chimeric thermostable DNA polymerase was tested for the ability to correct a 3'-primer mismatch during PCR. Chimeric polymerase trials were run in parallel with wild type Taq DNA polymerase and Pfu DNA polymerase I. The Taq DNA polymerase trials served as a negative control, representing a DNA polymerase possessing an enzymatically inactive 3'-5' exonuclease domain (i.e., proofreading capability). The Pfu DNA polymerase I trials served as a positive control, representing a thermostable DNA polymerase possessing an enzymatically active 3'-5' exonuclease domain.

PCR mixtures comprised 20 ng plasmid pQE-31 containing the (target) Taq polymerase gene sequence; 0.5 units of the test DNA polymerase; 0.4 µM of the appropriate trial primers (wild type vs. mutant primers); 200 µM of each dNTP; 1×Qiagen PCR buffer (Qiagen, Valencia, Calif.) or 1×Pfu reaction buffer (Stratagene, La Jolla, Calif.) and 1.5 mM $MgCl_2$ in a final reaction volume of 50 µl.

PCR was performed using a MJ Research PTC-200 Thermocycler (Biozym, Hess. Oldendorf, Germany) or a Biometra Unoll Thermocycler (Biometra, Göttingen, Germany). The PCR program consisted of an initial 1 min template denaturation step at 94° C. followed by 40 cycles of a 30 sec. denaturation step 94° C.; a 30 sec. annealing step at 62° C.; and a 1 min. polymerization step at 72° C. for 1 min. The PCR concluded with a final prolonged extension step for 2 min. at 72° C.

PCR products were analyzed on a 2% agarose gel by gel electrophoresis (approximately 35 min. at 85 volts) in 1×TAE electrophoresis buffer and Ethidium bromide. PCR products were visualized using UV irradiation, and quantified using the 200 bp DNA fragment of the Low DNA MassSONDZEICHEN™ Ladder (Life Technologies, Gaithersburg, Md., USA) as standard by gel densitometry. PCR products were purified using QIAquick™ PCR Purification Kit (Qiagen, Valencia, Calif.).

Figure 3:
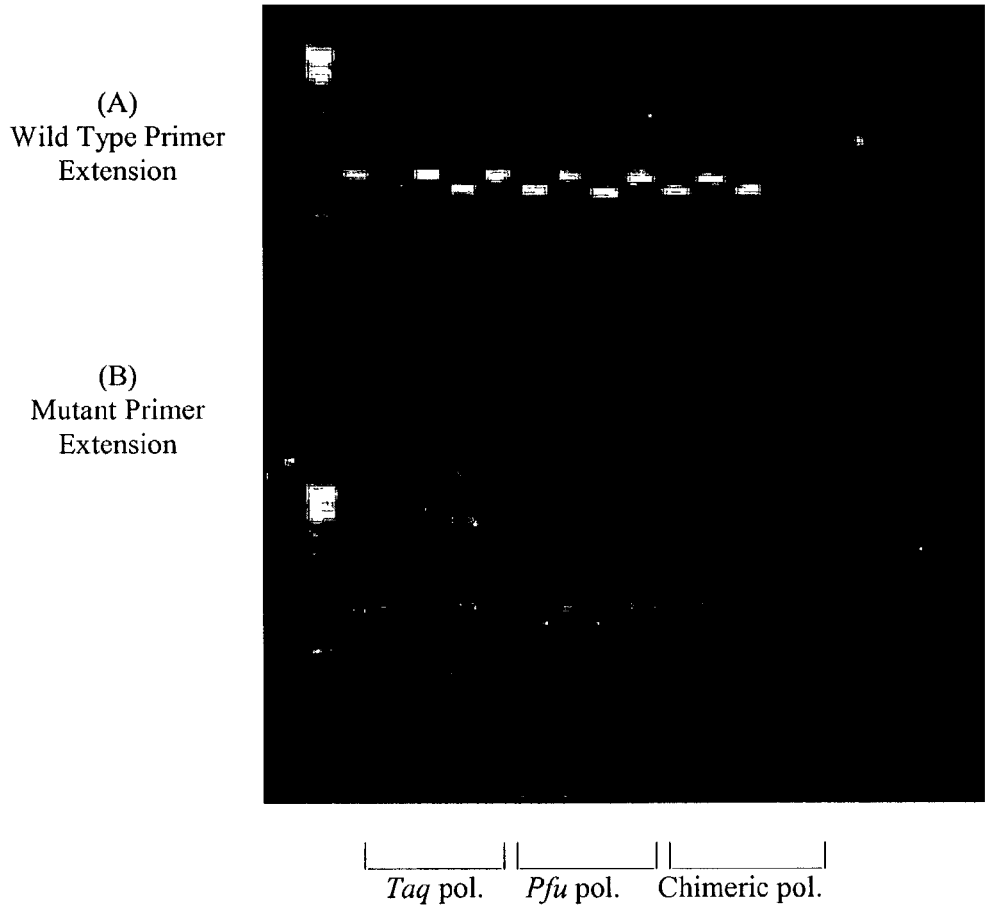
FIG. 3 is a photograph of an ethidium bromide (EtdBr)-stained agarose gel, which depicts 3'-5' exonuclease activity of three different thermostable DNA polymerases. (A) illustrates PCR product using a wild type primer combination. (B) illustrates PCR product using a mutant primer pair. Lane 1 is a nucleic acid ladder, used as a gel reference marker. The PCR amplification product of Taq DNA polymerase is shown in lanes 2-5; Pfu DNA polymerase I PCR product is shown in lanes 6-9; and a Pho/Taq thermostable chimeric DNA polymerase PCR product is shown in lanes 10-13. Duplicate side-by-side reactions are shown representing undigested (the first and third lane for each enzyme used), and digested (the second and fourth lane for each enzyme used) PCR product.

Identical amounts of PCR product were digested in the same final reaction volume using 1 unit BamHI (Life Technologies, Gaithersburg, Md., USA) per 100 ng PCR product and corresponding reaction buffer. Restriction digest was performed for 90 min. at 37° C. Digestion products were analyzed on a 4% Metaphor$^{SONDZEICHEN}$® agarose gel (Biozym, Hess. Oldendorf, Germany). FIG. 3. is representative of the results of the 3'-5' exonuclease activity assay.

FIG. 3(A) illustrates the PCR product of the three nucleic acid polymerases (Taq polymerase, Pfu polymerase, and the thermostable chimeric polymerase) using wild type primers. Alternating lanes represent undigested PCR product and PCR product subjected to BamHI digestion. Undigested product shows the intact 151 bp PCR product. Digestion treated product shows the 132 bp digestion fragment.

FIG. 3(B) illustrates the PCR product of the three polymerases (Taq polymerase, Pfu polymerase, and the thermostable chimeric polymerase) using mutant primers. Once again, alternating lanes represent undigested PCR product and PCR product subjected to BamHI digestion. Taq polymerase PCR product was unaffected by BamHI digestion (lanes 3 and 5), due to the lack of a BamHI site resulting for normal extension of the mutant primer. Pfu polymerase PCR product was effectively digested by BamHI (lanes 7 and 9), producing the expected 132 bp digestion fragment. These results are indicative of the proofreading ability (i.e., 3'-5' exonuclease activity) of Pfu polymerase, which corrected the nucleotide mismatch of the mutant primer, thus restoring the BamHI site of the template DNA.

The thermostable chimeric polymerase PCR product displayed results similar to the Pfu polymerase PCR product. The chimeric polymerase PCR product was also effectively digested by BamHI (lanes 11 and 13), producing the expected 132 bp digestion fragment and indicative of polymerase proofreading ability. These results confirm that the thermostable chimeric polymerase, which possesses the 5'-3' polymerase domain of Taq polymerase, also possesses an enzymatically active 3'-5' exonuclease domain not naturally occurring in Taq polymerase.

EXAMPLE 8

PCR Efficiency of Thermostable Chimeric DNA Polymerases

PCR efficiency of a DNA polymerase can be described as the combined effect of primer extension activity and processivity of the enzyme. PCR efficiency of the thermostable chimeric DNA polymerase was tested in comparison with Taq DNA polymerase, known to possess a higher PCR efficiency than common proofreading polymerases, and Pfu DNA polymerase (both serving as controls).

One unit of the respective polymerase was used to amplify a 750 bp large product from human genomic DNA using a thermocycling profile with varying primer extension times at 72° C. Limiting primer extension time was used to measure polymerase efficiency in PCR, using the same amount of enzyme activity in the assay. Taq DNA polymerase was assayed in its optimized PCR buffer (Qiagen, Valencia, Calif.), a Pho/Taq thermostable chimeric DNA polymerase was used in a 1×buffer consisting of 50 mM TrisHCl (pH 8.9 at room temperature), 10 mM $(NH_4)_2SO_4$, and Pfu DNA polymerase was used in the reaction buffer supplied with the enzyme (Stratagene, La Jolla, Calif.). All reactions contained 1 unit of enzyme, 0.4 µM of each primer, 200 µM of each dNTP, and a final $MgCl_2$ concentration of 1.5 mM (Taq polymerase, chimeric DNA polymerase) or 2.0 mM (Pfu polymerase).

Thermocycling was performed in a Biometra Uno thermocycler using the following cycling conditions: initial denaturation at 94° C. for 3 min followed by a denaturation step at 94° C. for 30 sec, an annealing step at 60° C. for 30 sec, and a primer extension step at 72° C. for 1 min, 30 sec, 10 sec or 5 sec. The reaction proceeded for 34 cycles, and concluded with a final extension step at 72° C. for 10 min.

Figure 4:
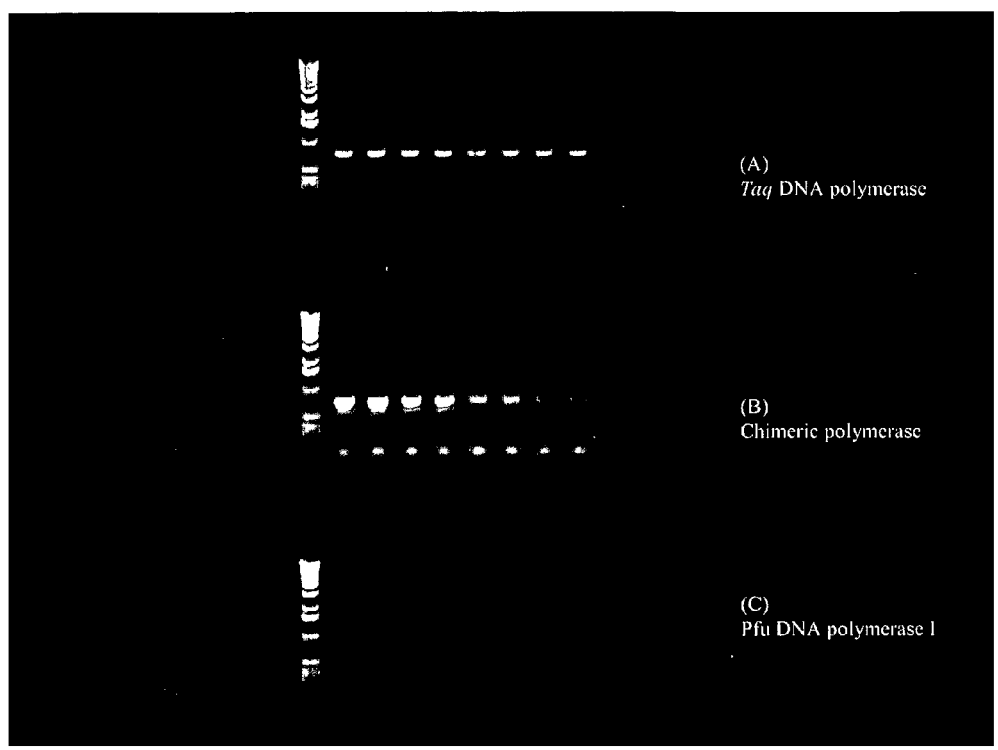
FIG. 4 is a photograph of an ethidium bromide (EtdBr)-stained agarose gel, which illustrates the combined effect of primer extension efficiency and polymerase processivity on PCR efficiency of three different thermostable DNA polymerases. The photograph illustrates PCR products obtained in duplicate reactions using different primer extension times. (A) indicates PCR products obtained with Taq DNA polymerase. (B) illustrates PCR products obtained with a Pho/Taq thermostable chimeric DNA polymerase. (C) shows PCR products generated with Pfu DNA polymerase I. Lane 1 is a nucleic acid ladder, used as a gel reference marker. Lanes 2-3 show PCR products amplified after primer extension for 1 min. Lanes 4-5 show PCR products amplified after primer extension for 30 sec. Lanes 6-7 show PCR products amplified after primer extension for 10 sec. Lanes 8-9 show PCR products amplified after primer extension for 5 sec.

The results are depicted in FIG. 4. Taq DNA polymerase (A) shows a high PCR efficiency even when primer extension time is as low as 5 sec. The thermostable chimeric DNA polymerase (B) shows a higher PCR efficiency than Taq polymerase at extension times of 1 min and 30 sec, but a slightly lower efficiency than Taq polymerase at 5 sec extension time. Pfu DNA polymerase I (C) generates a visible PCR product only when using the 1 min extension time.

These results indicate that the overall processivity of the chimeric polymerase is comparable to that of Taq DNA polymerase, and is dramatically better than Pfu DNA polymerase I. The thermostable chimeric polymerase of the present invention performs as well as Taq DNA polymerase (the standard enzyme of PCR protocols), and outperforms Pfu DNA polymerase I (the standard enzyme for high fidelity PCR protocols). In addition, the thermostable chimeric polymerase of the present invention combines the beneficial features of each of the standard enzymes for PCR protocols formerly not obtained with either Taq DNA polymerase or proofreading polymerases: removal of misincorporated nucleotides required for high fidelity PCR, and high PCR efficiency.

REFERENCES

Barnes, *PNAS USA* 91:2216-2220 (1994).
Barnes. U.S. Pat. No. 5,436,149 (1995).

Bedford et al., WO 97/29209 (Aug. 14, 1997).
Bernard et al., Cell 59:219 (1989).
Eom et al., Nature 382: 278-281 (1996)
Flaman et al. N.A.R. 22:3259-3260 (1994).
Frey et al., WO 99/47649 (Sep. 23, 1999).
Gelfand et al. U.S. Pat. No. 4,889,818 (1989).
Gelfand et al. U.S. Pat. No. 5,079,352 (1992).
Gelfand et al. U.S. Pat. No. 5,491,086 (1996).
Gelfand et al., EP 0 892 058 A2 (Jan. 20, 1999).
Gyllensten et al. U.S. Pat. No. 5,066,584 (1991).
Ho et al. U.S. Pat. No. 5,023,171 (1991).
Innes et al. U.S. Pat. No. 5,075,216 (1991).
Innes. U.S. Pat. No. 5,091,310 (1992).
Jacobson et al., Eur. J. Biochem. 45:623 (1974).
Joyce and Grindley, PNAS USA 80:1830 (1983).
Joyce and Steitz, Annu. Rev. Biochem. 63:777-822 (1994).
Kiefer et al., Structure 5: 95-108 (1997).
Klenow and Henningsen, PNAS USA 65:168 (1970).
Longley et al. N.A.R. 18:7317-7322 (1990).
Lawyer et al., J. Biol. Chem. 264:6427-6437 (1989).
Mendelman et al., J. Biol. Chem. 265(4):2338-2346 (1990).
Mullis et al. U.S. Pat. No. 4,683,195 (1987).
Mullis, U.S. Pat. No. 4,683,202 (1987).
Mullis et al. U.S. Pat. No. 4,800,159 (1989).
Mullis et al. U.S. Pat. No. 4,965,188 (1990).
Park et al., Mol. Cells 7(3):419-424 (1997).
Petruska et al., PNAS USA 85:6252-6256 (1988).
Silver et al. U.S. Pat. No. 5,104,792 (1992).

Each of the publications mentioned herein is incorporated by reference.

---

We claim:

1. A chimeric nucleic acid polymerase, comprising the amino acid sequence of SEQ ID NO. 3 and the amino acid sequence of SEQ ID NO. 1, wherein said chimeric nucleic acid polymerase exhibits 3'-5' exonuclease activity and 5'-3' polymerase activity, and wherein said chimeric nucleic acid polymerase retains at least about 95% of its polymerase activity at its normal operating temperature after exposure to 95° C. for three minutes.

2. A chimeric nucleic acid polymerase, comprising the amino acid sequence of SEQ ID NO. 3 and the amino acid sequence of SEQ ID NO. 7, wherein said chimeric nucleic acid polymerase exhibits 3'-5' exonuclease activity and 5'-3' polymerase activity, and wherein said chimeric nucleic acid polymerase retains at least about 95% of its polymerase activity at its normal operating temperature after exposure to 95° C. for three minutes.

3. A chimeric nucleic acid polymerase, comprising the amino acid sequence of SEQ ID NO. 4 and the amino acid sequence of SEQ ID NO. 1, wherein said chimeric nucleic acid polymerase exhibits 3'-5' exonuclease activity and 5'-3 'polymerase activity, and wherein said chimeric nucleic acid polymerase retains at least about 95 % of its polymerase activity at its normal operating temperature after exposure to 95° C. for three minutes.

4. A chimeric nucleic acid polymerase, comprising the amino acid sequence of SEQ ID NO. 5 and the amino acid sequence of SEQ ID NO. 1, wherein said chimeric nucleic acid polymerase exhibits 3'-5' exonuclease activity and 5'-3' polymerase activity, and wherein said chimeric nucleic acid polymerase retains at least about 95% of its polymerase activity at its normal operating temperature after exposure to 95° C. for three minutes.

5. A chimeric nucleic acid polymerase, comprising the amino acid sequence of SEQ ID NO. 4 and the amino acid sequence of SEQ ID NO. 7, wherein said chimeric nucleic acid polymerase exhibits 3'-5' exonuclease activity and 5'-3' polymerase activity, and wherein said chimeric nucleic acid polymerase retains at least about 95% of its polymerase activity at its normal operating temperature after exposure to 95° C. for three minutes.

6. A chimeric nucleic acid polymerase, comprising the amino acid sequence of SEQ ID NO. 6 and the amino acid sequence of SEQ ID NO. 1, wherein said chimeric nucleic acid polymerase exhibits 3'-5' exonuclease activity and 5'-3' polymerase activity, and wherein said chimeric nucleic acid polymerase retains at least about 95% of its polymerase activity at its normal operating temperature after exposure to 95° C. for three minutes.

7. A chimeric nucleic acid polymerase, comprising the amino acid sequence of SEQ ID NO. 6 and the amino acid sequence of SEQ ID NO. 7, wherein said chimeric nucleic acid polymerase exhibits 3'-5' exonuclease activity and 5'-3' polymerase activity, and wherein said chimeric nucleic acid polymerase retains at least about 95% of its polymerase activity at its normal operating temperature after exposure to 95° C. for three minutes.

8. A chimeric nucleic acid polymerase, comprising the amino acid sequence of SEQ ID NO. 16 and the amino acid sequence of SEQ ID NO. 1, wherein said chimeric nucleic acid polymerase exhibits 3'-5' exonuclease activity and 5'-3' polymerase activity, and wherein said chimeric nucleic acid polymerase is thermostable.

9. A chimenc nucleic acid polymerase, compnsing the amino acid sequence of SEQ ID NO. 16 and the amino acid sequence of SEQ ID NO. 7, wherein said chimeric nucleic acid polymerase exhibits 3'-5' exonuclease activity and 5'-3' polymerase activity, and wherein said chimeric nucleic acid polymerase is thermostable.

10. A chimeric nucleic acid polymerase, comprising the amino acid sequence of SEQ ID NO. 3 and the amino acid sequence of SEQ ID NO. 2, wherein said chimeric nucleic acid polymerase exhibits 3'-5' exonuclease activity and 5°-3° polymerase activity, and wherein said chimeric nucleic acid polymerase retains at least about 95% of its polymerase activity at its normal operating temperature after exposure to 95° C. for three minutes.

11. A thermostable chimeric nucleic acid polymerase, comprising a polypeptide selected from the group consisting of SEQ ID NO. 8; SEQ ID NO. 9 ; SEQ ID NO. 10 ; SEQ ID NO. 11 ; SEQ ID NO. 12 ; and SEQ ID NO. 17, wherein said chimeric nucleic acid polymerase exhibits 3'-5' exonuclease activity and 5'-3' polymerase activity, and wherein said chimeric nucleic acid polymerase retains at least about 95% of its polymerase activity at its normal operating temperature after exposure to 95° C. for three minutes.

12. A thermostable chimeric nucleic acid polymerase comprising:
(a) an enzymatically active 3'-5' exonuclease domain of a thermostable DNA polymerase selected from the group consisting of *Pyrococcus horikoshii* (Pho) polymerase, *Pyrococcus woesei* (Pwo) polymerase, *Sulfolobus solfa-* taricus (Sso) polymerase, *Thermococcus pacificus* (Tpac) polymerase, *Thermococcus litoralis* (TU) polymerase, *Thermatoga maritima* (Tma) polymerase, Pyrococcusfuriosus (Pfu) polymerase, Pyrococcus species strain KOD1 (KOD) polymerase, and Pyrococcus species strain ES4 (ES4) polymerase; and (b) an enzymatically active 5'-3' polymerase domain comprising a Stoffel fragment of Taq DNA polymerase comprising the sequence of amino acid residues 9 -552 of SEQ ID NO: 1, wherein said chimeric nucleic acid polymerase retains at least about 95 % of its polymerase activity at its normal operating temperature after exposure to 95 ° C. for three minutes.

13. The chimeric nucleic acid polymerase of claim 12, wherein said enzymatically active 5'-3' polymerase domain comprises the amino acid sequence of SEQ ID NO:1.

14. The chimeric nucleic acid polymerase of claim 12, wherein said enzymatically active 5'-3' polymerase domain comprises the amino acid sequence of SEQ ID NO:7.

15. A thermostable chimeric nucleic acid polymerase comprising:

(a) an enzymatically active 3'-5' exonuclease domain of a thermostable DNA polymerase selected from the group consisting of *Pyrococcus horikoshii* (Pho) polymerase, *Pyrococcus woesei* (Pwo) polymerase, *Sulfolobus solfataricus* (Sso) polymerase, *Thermococcus pacificus* (Tpac) polymerase, *Thermococcus litoralis* (TN polymerase, *Thermatoga maritime* (Tma) polymerase, Pyrococcusfuriosus (Pfu) polymerase, Pyrococcus species strain KOD1 (KOD) polymerase, and Pyrococcus species strain ES4 (ES4) polymerase; and (b) an enzymatically active 5'-3 polymerase domain comprising the sequence of amino acid residues of SEQ ID NO:2, wherein said chimeric nucleic acid polymerase retains at least about 95 % of its polymerase activity at its normal operating temperature after exposure to 95 ° C. for three minutes.

16. The chimeric nucleic acid polymerase of any one of claims 12-15, wherein said enzymatically active 3'-5' exonuclease domain includes the sequence of amino acid residues of SEQ ID NO:3.

17. The chimeric nucleic acid polymerase of any one of claims 12-15, wherein said enzymatically active 3'-5' exonuclease domain includes the sequence of amino acid residues of SEQ ID NO:4.

18. The chimeric nucleic acid polymerase of any one of claims 12-15, wherein said enzymatically active 3'-5' exonuclease domain includes the sequence of amino acid residues of SEQ ID NO:5.

19. The chimeric nucleic acid polymerase of any one of claims 12-15 wherein said enzymatically active 3'-5' exonuclcase domain includes the sequence of amino acid residues of SEQ ID NO:6.

20. The chimeric nucleic acid polymerase of any one of claims 12-15, wherein said enzymatically active 3'-5' exonuclease domain includes the sequence of amino acid residues of SEQ ID NO: 16.

21. the chimeric nucleic acid polymerase of any one of claims 1-7, 10, 12 and 15, wherein said chimeric nucleic acid polymerase retains at least about 50 % of its polymerase activity at its normal operating temperature after exposure to 90 ° C. for ten minutes.

\* \* \* \* \*